US012616709B2

(12) United States Patent
Yu et al.

(10) Patent No.: US 12,616,709 B2
(45) Date of Patent: May 5, 2026

(54) PHARMACEUTICAL COMPOSITION FOR TREATING SEPSIS AND USE THEREOF

(71) Applicant: TIANJIN CHASE SUN PHARMACEUTICAL CO., LTD., Tianjin (CN)

(72) Inventors: Yang Yu, Tianjin (CN); Jianli Wang, Tianjin (CN); Chunliang Jiang, Tianjin (CN); Xiangcheng Wang, Tianjin (CN); Yukun Li, Tianjin (CN); Baoqi Li, Tianjin (CN); Guiping Zhang, Tianjin (CN); Kai Dong, Tianjin (CN); Xiaoqing Yao, Tianjin (CN)

(73) Assignee: TIANJIN CHASE SUN PHARMACEUTICAL CO., LTD., Tianjin (CN)

( * ) Notice: Subject to any disclaimer, the term of this patent is extended or adjusted under 35 U.S.C. 154(b) by 385 days.

(21) Appl. No.: 18/272,466

(22) PCT Filed: Mar. 23, 2021

(86) PCT No.: PCT/CN2021/082244

§ 371 (c)(1),
(2) Date: Jul. 14, 2023

(87) PCT Pub. No.: WO2022/183539

PCT Pub. Date: Sep. 9, 2022

(65) Prior Publication Data

US 2024/0307425 A1 Sep. 19, 2024

(30) Foreign Application Priority Data

Mar. 1, 2021 (CN) ......................... 202110225428.6

(51) Int. Cl.
*A61K 31/7048* (2006.01)
*A61K 31/192* (2006.01)
*A61K 31/365* (2006.01)
*A61K 31/70* (2006.01)
*A61P 37/06* (2006.01)

(52) U.S. Cl.
CPC ........ *A61K 31/7048* (2013.01); *A61K 31/192* (2013.01); *A61K 31/365* (2013.01); *A61K 31/70* (2013.01); *A61P 37/06* (2018.01)

(58) Field of Classification Search
USPC ............................................................ 514/27
See application file for complete search history.

(56) References Cited

U.S. PATENT DOCUMENTS 11,968,553 B2 * 4/2024 Usaj ................ H04N 21/44222
2019/0269609 A1 * 9/2019 Yao ..................... A61K 31/198

FOREIGN PATENT DOCUMENTS

| | | | |
|---|---|---|---|
| CN | 1432391 | A | 7/2003 |
| CN | 101317893 | A | 12/2008 |
| CN | 105181848 | A | 12/2015 |
| CN | 105241980 | A | 1/2016 |
| CN | 106727649 | A | 5/2017 |
| CN | 106950307 | A | 7/2017 |
| CN | 108508107 | A | 9/2018 |
| CN | 108743600 | A | 11/2018 |
| CN | 109260214 | A | 1/2019 |
| CN | 109394750 | A | 3/2019 |
| CN | 109709244 | A | 5/2019 |
| CN | 110632230 | A | 12/2019 |
| CN | 110907576 | A | 3/2020 |

OTHER PUBLICATIONS

Kai Dong, et al, "Research Advances in Sepsis and Treatments Therefor," Tianjin Hongri Pharmaceutical Co., Ltd.and The Third Military Medical University of the People's Liberation Army, undated.

Qun Liang et al, "Research Progress of Xuebijing Injection in Treatment of Sepsis," Tianjin Journal of Traditional Chinese Medicine, Jul. 2019, vol. 36, No. 7, (English Abstract).

International Search Report from corresponding PCT/CN2021/082244, dated Jul. 13, 2021.

Sun, M., et al, "Effect of Treatment with Xuebijing Injection and Its Pharmacokinetics Markers on Serum Inflammatory Factor Include TNF-a, IL-1, IL-6, IL-8, and IL-10 in Rats with Sepsis," Tianjin University of Traditional Chinese Medicine, China, Journal of Tianjin University of Traditional Chinese Medicine, vol. 37, No. 1, Feb. 2018.

Li, D., et al., "Research on Quality Control Method of Xuebijing Injection," Tianjin University of Traditional Medicine, China, Mod Chin Med, vol. 20, No. 9, Sep. 2018.

Using Pharmacokinetics to Search for Pharmacodynamic Substances of Xuebijing and Phthalides in Antisepsis Traditional Chinese Medicine Injection (undated).

(Continued)

*Primary Examiner* — Traviss C McIntosh, III
(74) *Attorney, Agent, or Firm* — Lando & Anastasi, LLP

(57) ABSTRACT

The present disclosure provides a pharmaceutical composition for treating sepsis and use thereof, belonging to the technical field of chemical drugs. The present disclosure provides a three-component pharmaceutical composition including hydroxysafflower yellow A (HSYA), paeoniflorin, and albiflorin. The present disclosure further provides a seven-component pharmaceutical composition including HSYA, paeoniflorin, albiflorin, oxypaeoniflorin, senkyunolide I, salvianic acid A sodium (SAAS), and ferulic acid. In the present disclosure, it is verified at the cell level and the animal level that both two groups of the pharmaceutical compositions have an efficacy of effectively treating sepsis. Meanwhile, drug toxicity experiments show that the two groups of the pharmaceutical compositions both are safe. The pharmaceutical composition is an active ingredient of the Xuebijing Injection, which can be used for the clinical treatment of sepsis.

10 Claims, No Drawings

(56) References Cited

OTHER PUBLICATIONS

Chinese First Office Action, in corresponding CN20210225428.6, titled "Pharmaceutical Composition for Treating Sepsis and Use Thereof.".
Xin-Tong Wang et al., "Paeoniflorin and Hydroxysafflor Yellow a in Xuebijing Injection Attenuate Sepsis-Induced Cardiac Dysfunction and Inhibit Proinflammatory Cytokine Production," Frontiers in Pharmacology, (/paper/journal/2179?r_detail=1382106124887547904), Pub. Date Dec. 7, 2020.
Yan-Yan Feng, et al., "Molecular Mechanism of Xuebijing Injection In Treatment of Sepsis According to "Drug-Target-Pathway" , "Network, School of Traditional Chinese Medicine, Department of Chemistry, China May 1, 2017.
Yinping Li et al., "Effect of Xuebijing Injection on Activated Protein C and Coagulation Function in Sepsis Rats," Tianjin Tianhe Hospital, Tianjin University of Traditional Chinese Medicin, The First Affiliated Hospital of the People's Liberation Army General Hospital, and the Military Burn Research Institute, undated.
Yongming Yao; "Exploration of a New Approach to the Treatment of Sepsis With Traditional Chinese Medicine Xuebijing Injection," The First Affiliated Hospital of the People's Liberation Army General Hospital and the Military Burn Research Institute, undated.
Lei Zhang, et al., "Characterization and Quantification of Major Constituents of Xue Fu Zhu Yu by UPLC-DAD-MS/MS," Journal of Pharmaceutical and Biomedical Analysis, Aug. 5, 2011.
Huang Hao et al, "Identification of the Major Constituents in Xuebijing Injection by HPLC-ESI-MS," Phyto Chemical Analysis, Published Wiley Online Library Apr. 15, 2011.
H. Huang et al., "Simultaneous Determination of Thirteen Main Components and Identification of Eight Major Metabolites in Xuebijing Injection by UPLCQ-TOF," Journal of Analytical Chemistry, vol. 68, No. 4 (2013).
Bibliography in Edition (CIP) Data Pharmacologiedical Publishing House, 2001 ISBN7-117-04494-1 1 with translation, cover and copyright page . . . .
Bibliography in Edition (CIP) Data Pharmacologiedical Publishing House, 2001 ISBN7-117-04494-1 1 with translation, Preface.
Yinlin, "Correcting Mistakes in the Medical Forest," undated.
Chinese First Office Action, in corresponding CN202110225428.6, titled "Pharmaceutical Composition for Treating Sepsis and Use Thereof.".

* cited by examiner

PHARMACEUTICAL COMPOSITION FOR TREATING SEPSIS AND USE THEREOF

CROSS-REFERENCE TO RELATED APPLICATIONS

This application is a U.S. National Phase Application under 35 U.S.C. § 371 of International Application No. PCT/CN2021/082244, filed on Mar. 23, 2021, which claims priority to Chinese Patent Application No. 202110225428.6, filed on Mar. 1, 2021, and titled "PHARMACEUTICAL COMPOSITION FOR TREATING SEPSIS AND USE THEREOF," the contents of which is incorporated by reference in its entirety.

TECHNICAL FIELD

The present disclosure belongs to the technical field of chemical drugs, and in particular relates to a pharmaceutical composition for treating sepsis and use thereof.

BACKGROUND

Sepsis is a fatal organ dysfunction caused by a dysregulated response to an infected host. The sepsis causes a dangerous condition and a high fatality rate, and is the main cause of death of the severe patients. Antibiotics, antivirals, and vasopressors have been used in the traditional treatment of sepsis for many years. However, there are not enough specific drugs targeting the pathogenesis of sepsis in clinical practices. Timely remedy of systemic inflammatory response, coagulation dysfunction, and immune dysfunction during the progress of sepsis has become an important topic to be address in the research and development of therapeutic drugs for the sepsis. This can help to restore a pro-inflammatory/anti-inflammatory dynamic balance in the body as soon as possible, and effectively improve the prognosis of patients.

Xuebijing Injection is an intravenous injection. The Xuebijing Injection is based on the principle of syndrome differentiation of "Three syndromes and three methods" (namely. "toxin-heat syndrome" with "heat-clearing and detoxifying". "blood stasis syndrome" with "activating blood circulation and removing blood stasis", and "acute deficiency syndrome" with "strengthening and consolidating body resistance"), and under the guidance of a theory "combining the treatment of pathogenic bacteria, toxin, and inflammation". The Xuebijing Injection is developed with a "Xuefu Zhuyu Decoction (decoction for repelling blood stasis in blood vessels)" recorded in the "Yilin Gaicuo (Correction on Errors in Medical Classics)" written by Qingren Wang of the Qing Dynasty. This injection is prepared from five Chinese medicinal materials of *Carthamus tinctorius, Radix paeoniae rubra, Rhizoma chuanxiong, Radix salviae miltiorrhizae*, and *Radix angelicae sinensis* through modern processes such as extraction, refining, drying, and blending. This injection is suitable for sepsis/infection-induced systemic inflammatory response syndrome (SIRS), and can also be used in the treatment of organ dysfunction in multiple-organ dysfunction syndrome. However, the Xuebijing Injection is prepared from Chinese herbal medicines, and the main medicinal ingredients for sepsis are yet unclear. Therefore, it is still necessary to extract and refine various Chinese medicinal materials to prepare a pharmaceutical composition for treating sepsis.

SUMMARY

In view of this, an objective of the present disclosure is to provide a novel pharmaceutical composition for treating sepsis and use thereof. The pharmaceutical composition is directly consisting of active compounds for treating the sepsis, thus avoiding cumbersome extraction steps of traditional Chinese medicines. Moreover, in this way, the components of the pharmaceutical composition are simplified and the efficacy of an obtained product is improved.

The present disclosure provides a pharmaceutical composition for treating sepsis, including hydroxysafflor yellow A (HSYA) with a structural formula shown in formula I, paeoniflorin with a structural formula shown in formula II, and albiflorin with a structural formula shown in formula III; where HSYA, paeoniflorin, and albiflorin are present in a mass ratio of (1-100):(1-100):(0.1-10);

formula I

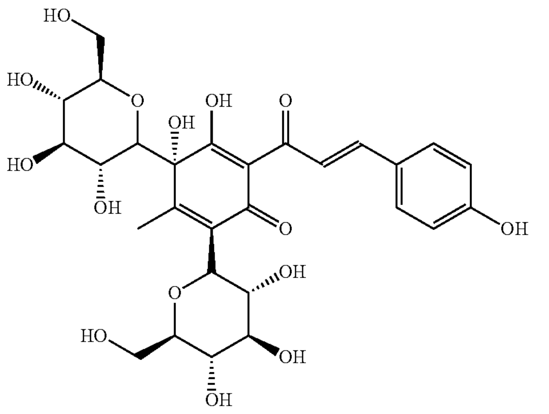

formula II

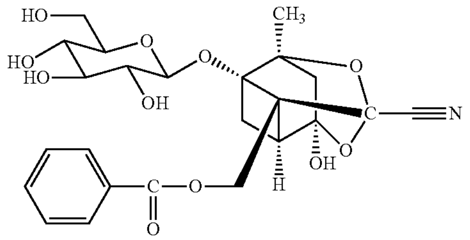

formula III

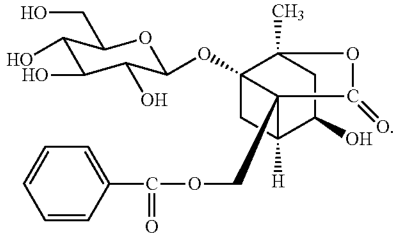

Preferably, HSYA, paeoniflorin, and albiflorin are present in a mass ratio of (1-100):(1-100):(1-10).

Preferably, the pharmaceutical composition for treating sepsis further includes oxypaeoniflorin with a structural formula shown in formula IV, senkyunolide I with a structural formula shown in formula V, salvianic acid A sodium (SAAS) with a structural formula shown in formula VI, and ferulic acid with a structural formula shown in formula VII; where the HSYA, the paeoniflorin, the albiflorin, the oxypaeoniflorin, the senkyunolide I, the SAAS, and the ferulic are a mass acid present in ratio of (1-100):(1-100):(1-10):(0.1-10):(0.1-10):(0.1-10):(0.01-1);

formula IV

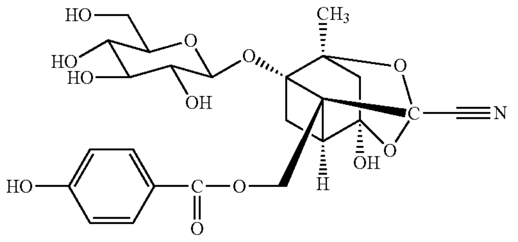

formula V

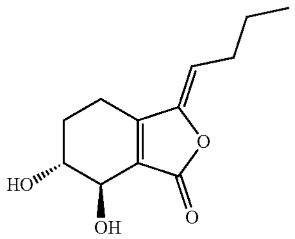

formula VI

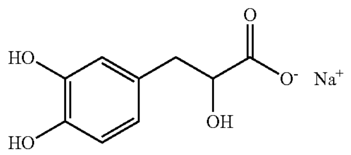

formula VII

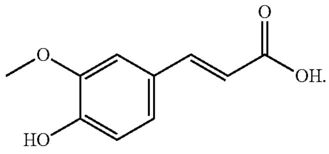

Preferably, the HSYA, the paeoniflorin, the albiflorin, the oxypaeoniflorin, the senkyunolide I, the SAAS, and the ferulic acid are present in a mass ratio of (1-100):(1-100):(1-10):(1-10):(1-10):(1-10):(0.1-1).

The present disclosure further provides use of the pharmaceutical composition in preparation of a drug for treating sepsis.

Preferably, the pharmaceutical composition is used in preparing a drug for treating sepsis by inhibiting expressions of IL-6, Foxp3, CTLA-4, and/or HMGB1.

Preferably, the pharmaceutical composition is used in preparing a drug for treating sepsis by inhibiting release of tissue factor (TF) and/or thrombomodulin (TM).

Preferably, the pharmaceutical composition is used in preparing a drug for treating sepsis by promoting apoptosis of regulatory T cells.

Preferably, when the pharmaceutical composition includes three active compounds of the HSYA, the paeoniflorin, and the albiflorin, 6 mg/kg to 600 mg/kg of the HSYA, 6 mg/kg to 600 mg/kg of the paeoniflorin, and 0.6 mg/kg to 60 mg/kg of the albiflorin are used.

Preferably, when the pharmaceutical composition includes seven active compounds of the HSYA, the paeoniflorin, the albiflorin, the oxypaeoniflorin, the senkyunolide I, the SAAS, and the ferulic acid, 6 mg/kg to 600 mg/kg of the HSYA, 6 mg/kg to 600 mg/kg of the paeoniflorin, 0.6 mg/kg to 60 mg/kg of the albiflorin, 0.6 mg/kg to 60 mg/kg of the oxypaeoniflorin, 0.6 mg/kg to 60 mg/kg of the senkyunolide I, 0.6 mg/kg to 60 mg/kg of the SAAS, and 0.06 mg/kg to 6 mg/kg of the ferulic acid are used.

The present disclosure further provides a method for treating sepsis, including administering a drug prepared from the pharmaceutical composition.

Preferably, the pharmaceutical composition treats the sepsis by inhibiting expressions of IL-6, Foxp3, CTLA-4, and/or HMGB1 in patients with sepsis.

Preferably, the pharmaceutical composition treats the sepsis by inhibiting release of TF and/or TM in patients with sepsis.

Preferably, the pharmaceutical composition treats the sepsis by promoting apoptosis of regulatory T cells in patients with sepsis.

Preferably, when the pharmaceutical composition includes three active compounds of the HSYA, the paeoniflorin, and the albiflorin, 6 mg/kg to 600 mg/kg of the HSYA, 6 mg/kg to 600 mg/kg of the paeoniflorin, and 0.6 mg/kg to 60 mg/kg of the albiflorin are used.

Preferably, when the pharmaceutical composition includes seven active compounds of the HSYA, the paeoniflorin, the albiflorin, the oxypaeoniflorin, the senkyunolide I, the SAAS, and the ferulic acid, 6 mg/kg to 600 mg/kg of the HSYA, 6 mg/kg to 600 mg/kg of the paeoniflorin, 0.6 mg/kg to 60 mg/kg of the albiflorin, 0.6 mg/kg to 60 mg/kg of the oxypaeoniflorin, 0.6 mg/kg to 60 mg/kg of the senkyunolide I, 0.6 mg/kg to 60 mg/kg of the SAAS, and 0.06 mg/kg to 6 mg/kg of the ferulic acid are used.

The present disclosure provides a pharmaceutical composition for treating sepsis, including HSYA with a structural formula shown in formula I, paeoniflorin with a structural formula shown in formula II, and albiflorin with a structural formula shown in formula III; where the HSYA, the paeoniflorin, and the albiflorin are present in a mass ratio of (1-100):(1-100):(0.1-10). In the present disclosure, it is confirmed at the cell level and animal level that the pharmaceutical composition inhibits expressions of IL-6, HMGB1, CTLA-4, and Foxp3 in macrophages in the sepsis, effectively inhibits releases of TF and TM in the sepsis, and promotes apoptosis of regulatory T lymphocytes. These indicate that the pharmaceutical composition has a significant effect on correcting the immunosuppressive state of cells or body cells for sepsis, thereby treating the sepsis.

Meanwhile, in the present disclosure, the pharmaceutical composition has been subjected to an acute toxicity test of intravenous administration. The results show that animals have no obvious abnormality after administration, a body weight and a weight growth rate of the animals are not significantly different from those in a control group, and no obvious abnormality is found in the gross anatomy. This shows that the pharmaceutical composition has drug safety.

Further, the pharmaceutical composition for treating sepsis further includes oxypaeoniflorin with a structural formula shown in formula IV, senkyunolide I with a structural formula shown in formula V, salvianic acid A sodium (SAAS) with a structural formula shown in formula VI, and ferulic acid with a structural formula shown in formula VII; where the HSYA, the paeoniflorin, the albiflorin, the oxypaeoniflorin, the senkyunolide I, the SAAS, and the ferulic acid ratio are present in a mass of (1-100):(1-100):(0.1-10):(0.1-10):(0.1-10):(0.1-10):(0.01-1). The HSYA is identified as an active ingredient of *Carthamus tinctorius* for treating sepsis. The paeoniflorin, the albiflorin, and the oxypaeoniflorin are active ingredients of *Radix paeoniae rubra* and *Radix paeoniae alba* in treating sepsis. The senkyunolide I is an active ingredient in *Rhizoma chuanxiong* and *Radix angelicae sinensis* for treating sepsis. The tanshinol is present as an active ingredient of *Radix aalviae miltiorrhizae* in treating sepsis. The ferulic acid is an active ingredient of *Radix angelicae sinensis* in the treatment of sepsis. The above seven active ingredients are strictly dose-proportioned to prepare a pharmaceutical composition. Compared with a pharmaceutical composition composed of three compounds, the seven-component pharmaceutical composition has a stronger inhibitory effect on the expressions of IL-6, HMGB1, CTLA-4, and Foxp3 in macrophages in sepsis, a stronger inhibitory effect on the releases of TF and TM in sepsis, and a stronger promotion effect on the apoptosis of regulatory T lymphocytes. Experiments show that the pharmaceutical composition has stronger efficacy in treating the sepsis and achieves a better therapeutic effect.

Meanwhile, in the present disclosure, the pharmaceutical composition containing seven active ingredients were subjected to an acute toxicity test through intravenous administration. The results showed that animals had no obvious abnormality after administration, a body weight and a weight growth rate of the animals were not significantly different from those in the control group, and no obvious abnormality was found in the gross anatomy. This shows that the pharmaceutical composition has drug safety.

DETAILED DESCRIPTION OF THE EMBODIMENTS

The present disclosure provides a pharmaceutical composition for treating sepsis, including hydroxysafflor yellow A (HSYA) with a structural formula shown in formula I, paeoniflorin with a structural formula shown in formula II, and albiflorin with a structural formula shown in formula III; where the HSYA, the paeoniflorin, and the albiflorin are present in a mass ratio of (1-100):(1-100):(0.1-10);

formula I

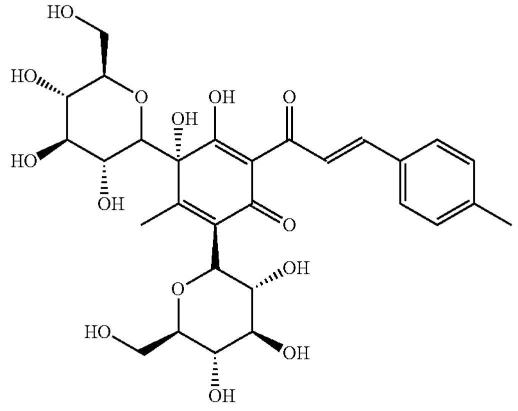

formula II

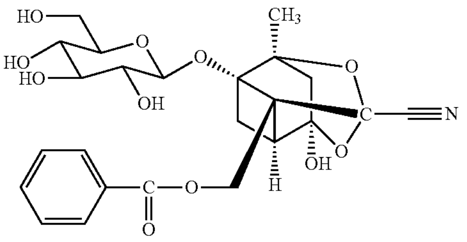

-continued formula III

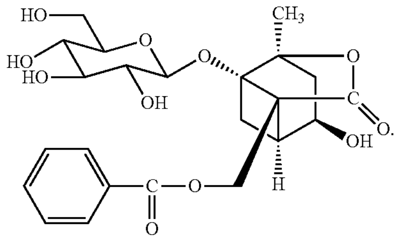

In the present disclosure, the HSYA, the paeoniflorin, and the albiflorin are present in a mass ratio of preferably (1-100):(1-100):(1-10), such as (1-100):1:1, (1-100):10:1, (1-100):100:1, (1-100):1:0.01, (1-100):1:10, (1-100):10:10, (1-100):10:1, and (1-100):10:0.01, specifically 1:10:10, 1:100:1, 10:1:10, 10:10:1, 10:100:0.1, 100:1:1, 100:10:0.1, and 10:10:1, most preferably 10:10:1. HSYA, with a molecular formula of $C_{27}H_3O_{16}$ and a molecular weight of 612.53, is an active ingredient of commonly-used traditional Chinese medicine *Carthamus tinctorius*. The HSYA is a compound with a single chalcone glycoside structure, and is the most effective water-soluble part of the pharmacological effects of *Carthamus tinctorius*. HSYA can inhibit platelet aggregation and release effects induced by a platelet activating factor, competitively inhibit the binding of the platelet activating factor with a platelet receptor, has anti-platelet and anti-myocardial ischemia effects, and is an active ingredient of safflor yellow for promoting blood circulation and removing blood stasis. In addition, the HSYA also has certain anti-inflammatory, cell protection, and anti-tumor activities. Paeoniflorin, with a molecular formula of $C_{23}H_{28}O_{11}$ and a molecular weight of 480.46, is an active ingredient of commonly-used traditional Chinese medicines *Radix paeoniae rubra* and *Radix paeoniae alba*. The paeoniflorin is a monoterpene glycoside compound with diverse pharmacological effects, including resisting damages caused by free radicals, inhibiting intracellular calcium overload, and resisting neurotoxicity. In vivo experiments have proved that the paeoniflorin has various biological effects such as reducing blood viscosity, dilating blood vessels, improving microcirculation, anti-oxidation, and anti-convulsions, and shows less toxic and side effects. Albiflorin has a molecular formula of $C_{23}H_{28}O_{11}$ and a molecular weight of 480.46. The albiflorin is similar in chemical structure to the paeoniflorin, is an isomer of the paeoniflorin, and has a lower content than that in the paeoniflorin. The albiflorin can act on hematopoietic cytokines in spleen and thymus in the immune system, and the blood system, and has a definite effect of enriching blood. Meanwhile, the albiflorin can also act on an HPA axis in the nervous system and the neurotransmitter of monoamines in the brain, and has an obvious antidepressant effect. The forms of the HSYA, albiflorin, and paeoniflorin include not only their compound monomers, but also preferably their pharmaceutically acceptable salts, solvates, polymorphs, enantiomers, or racemic mixtures.

In the present disclosure, the pharmaceutical composition for treating sepsis further includes preferably oxypaeoniflorin with a structural formula shown in formula IV, senkyunolide I with a structural formula shown in formula V, SAAS with a structural formula shown in formula VI, and ferulic acid with a structural formula shown in formula VII; where the HSYA, the paeoniflorin, the albiflorin, the oxypaeoniflorin, the senkyunolide I, the SAAS, and the ferulic acid are present in a mass ratio of (1-100):(1-100):(0.1-10):(0.1-10):(0.1-10):(0.1-10):(0.01-1);

formula IV

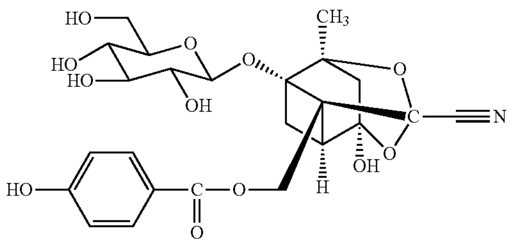

formula V

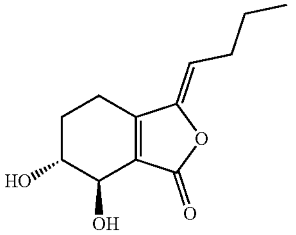

formula VI

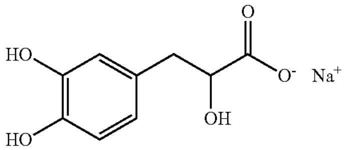

formula VII

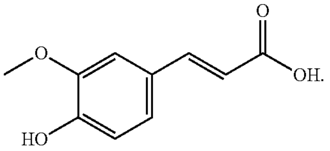

In the present disclosure, the HSYA, the paeoniflorin, the albiflorin, the oxypaeoniflorin, the senkyunolide I, the SAAS, and the ferulic acid are present in a mass ratio of preferably (1-100):(1-100):(1-10):(1-10):(1-10):(1-10):(0.1-1), specifically 1:10:1:1:1:1:0.1, 1:100:10:10:10:10:1, 10:1:0.1:1:1:10:1, 10:10:1:10:10:0.1:0.01, 10:100:10:0.1:0.1:1:0.1, 100:0.1:1:0.1:10:1:1, 100:10:0.1:10:1:0.1:10:0.01, 100:100:0.1:10:1:0.1:1, 1:1:10:10:1:1:0.01, 1:10:0.1:0.1:10:10:1, 1:100:1:1:0.1:0.1:1, 10:1:1:0.1:1:0.1:0.1, 10:10:10:10:0.1:0.1:1, 10:100:0.1:1:10:1:0.01, 100:1:10:1:10:0.1:1, 100:10:0.1:10:0.1:1:1, and 100:100:1:0.1:1:10:0.01, most preferably 100:100:1:0.1:1:10:0.01. A content of the oxypaeoniflorin is relatively low in the *Radix paeoniae rubra* and *Radix paeoniae alba*, and there are few reports on its pharmacological effects. Total glucosides in paeony have analgesic, anti-infection, anti-oxidation, and anti-cancer effects, show an extremely high application value, and are worthy of clinical promotion. Senkyunolide I is a phthalide compound isolated from the extracts of traditional Chinese medicines such as *Rhizoma chuanxiong* and *Radix angelicae sinensis*, has desirable fat solubility and water solubility, and has various pharmacological effects. The senkyunolide I can inhibit the NF-κB pathway, thereby exerting an anti-inflammatory effect. In vivo experiments have found that the senkyunolide I has a certain protective effect on ischemia-reperfusion injury (IRI). Moreover, the senkyunolide I can reduce the deformation index and pointing index of erythrocytes, reduce the aggregation of erythrocytes, and exhibit anticoagulant and antiplatelet-aggregation activities. Tanshinol is the main medicinal ingredient among the water-soluble components of *Radix salviae miltiorrhizae*, and is a phenolic aromatic acid compound. To increase stability, tanshinol is made into SAAS, which has the same efficacy as that of the tanshinol. Studies have shown that the tanshinol can reduce the scope of myocardial infarction and the course of disease, and reduce myocardial IRI, and has a protective effect on the myocardium. The tanshinol can also significantly inhibit the aggregation of platelets to reduce the viscosity of whole blood, has an anticoagulant effect that improves the microcirculation disturbance of various organs (such as heart, liver, and lung), and can contribute to the recovery of body tissues. In addition, the tanshinol also has certain antibacterial and anti-inflammatory effects and enhances the body's immunity. Ferulic acid is one of the medicinal ingredients of *Radix angelicae sinensis*, and belongs to phenolic acid compounds. The ferulic acid can anti-platelet aggregation, inhibits the release of 5-hydroxytryptamine of platelets, inhibits the generation of thromboxane A2 (TXA2) of platelets, enhances the activity of prostaglandins, relieves pains, and relieves vasospasm. Experiments have proved that the HSYA, paeoniflorin, albiflorin, oxypaeoniflorin, senkyunolide I, SAAS, and ferulic acid are effective components in the Xuebijing Injection, and show important practical significance and application value in sepsis treatment. The forms of the oxypaeoniflorin, senkyunolide I, SAAS, and ferulic acid include not only their compound monomers, but also preferably their pharmaceutically acceptable salts, solvates, polymorphs, enantiomers, or racemic mixtures.

In the present disclosure, a preparation method of the pharmaceutical composition includes preferably the following steps:

mixing the HSYA, the paeoniflorin, and the albiflorin according to the above mass ratio.

When the pharmaceutical composition includes 7 components, the preparation method includes preferably the following steps: mixing the HSYA, the paeoniflorin, the albiflorin, the oxypaeoniflorin, the senkyunolide I, the SAAS, and the ferulic acid according to the above mass ratio.

The present disclosure further provides use of the pharmaceutical composition in preparation of a drug for treating sepsis. The pharmaceutical composition is used in treating the sepsis.

In the present disclosure, the pharmaceutical composition is used preferably in preparing a drug for inhibiting expressions of IL-6. Foxp3, CTLA-4, and/or HMGB1 in patients with sepsis. The experimental results showed that a control group contained a small amount of IL-6 and HMGB1 at the cell level and animal level. The contents of IL-6, HMGB1, Foxp3, and CTLA-4 in a model group increased significantly. The plasma levels of IL-6, HMGB1, Foxp3, and CTLA-4 in a pharmaceutical composition administration group (8 h, 24 h, and 48 h) were significantly lower than those in the model group. A three-component-drug group in each dosage group could significantly reduce the expressions of IL-6, HMGB1, Foxp3, and CTLA-4 in CLP sepsis, suggesting that the drug had a significant inhibitory effect on the early inflammatory response of a rat model of sepsis. The pharmaceutical composition treats the early inflammatory response of the sepsis by inhibiting the expressions of IL-6, Foxp3, CTLA-4, and/or HMGB1.

In the present disclosure, the pharmaceutical composition is used preferably in preparing a drug for inhibiting release of TF and/or TM in patients with sepsis. Experiments show that there are certain expressions of TM and TF in monocytes in the control group at the cellular and animal levels. The expression of TM and TF (12 h, 24 h, 48 h, and 72 h after operation) in the model group are significantly higher than those in the control group ($p<0.05$), and gradually increase with the prolongation of postoperative time. The expression of TM and TF (12 h, 24 h, 48 h, and 72 h after operation) in the pharmaceutical composition administration group are significantly lower than those in the model group ($p<0.05$). This shows that the pharmaceutical composition can obviously inhibit the release of blood coagulation factors and improve the hypercoagulable state on the rat model of sepsis. The pharmaceutical composition treats the coagulation syndrome of sepsis by inhibiting the releases of TF and/or TM.

In the present disclosure, the pharmaceutical composition is used preferably in preparing a drug for promoting apoptosis of regulatory T cells (Tregs) in patient with sepsis. Experiments show that an apoptosis rate of Tregs in the model group is significantly lower than that in the control group ($p<0.05$), and an apoptosis rate of Tregs in the Chinese medicine composition administration group is significantly higher than that in the model group ($p<0.05$). Compared with the model group, the three-component drug group and the seven-component drug group of each dosage group can promote the apoptosis of Tregs in sepsis, and have an inhibitory effect of down-regulating the proliferation and secretion function of T lymphocytes. The pharmaceutical composition regulates the proliferation and secretion function of T lymphocytes by promoting the Treg apoptosis.

In the present disclosure, the pharmaceutical composition is subjected to drug experiments at the cell level and the animal level, respectively. On the basis of a dosage for animals, according to the calculation of body surface area conversion between human and animal in "*Pharmacological Experimental Methodology*" authored by Shuyun Xu, a dosage for human is calculated according to Formula A:

Human dosage=Rat dosage/0.018 Formula A.

In this formula, the body weight of an adult is 70 kg, and that of a rat is 0.2 kg.

In the present disclosure, when the pharmaceutical composition includes preferably three active compounds of the HSYA, the paeoniflorin, and the albiflorin, 6 mg/kg to 600 mg/kg of the HSYA, 6 mg/kg to 600 mg/kg of the paeoniflorin, and 0.6 mg/kg to 60 mg/kg of the albiflorin are used. In the present disclosure, when the pharmaceutical composition includes preferably seven active compounds of the HSYA, the paeoniflorin, the albiflorin, the oxypaeoniflorin, the senkyunolide I, the SAAS, and the ferulic acid, 6 mg/kg to 600 mg/kg of the HSYA, 6 mg/kg to 600 mg/kg of the paeoniflorin, 0.6 mg/kg to 60 mg/kg of the albiflorin, 0.6 mg/kg to 60 mg/kg of the oxypaeoniflorin, 0.6 mg/kg to 60 mg/kg of the senkyunolide I, 0.6 mg/kg to 60 mg/kg of the SAAS, and 0.06 mg/kg to 6 mg/kg of the ferulic acid are used.

In the present disclosure, there is no special limitation on a dosage form of the drug, and a pharmaceutical dosage form well known in the art can be used. For example, the dosage forms include tablets, capsules, oral liquids, granules, dissolved granules, pills, powders, ointments, elixirs, suspensions, solutions, injections, suppositories, sprays, and drops. There is no special limitation on a preparation method of each dosage form of the drug, and preparation methods of pharmaceutical dosage forms well known in the art can be used.

The pharmaceutical composition for treating sepsis and use thereof provided by the present disclosure are described in detail below with reference to the examples, but these examples should not be understood as limiting the claimed scope of the present disclosure.

EXAMPLE 1

1. Experimental Materials

Clean-grade SD rats (half male and half female), 180 g to 220 g; HSYA, paeoniflorin, albiflorin, and SAAS purchased from Shanghai Tauto Biotech Co., Ltd.; oxypaeoniflorin, senkyunolide I, and ferulic acid purchased from Shanghai Sunny Biotech Co., Ltd.; normal saline (0.9% sodium chloride injection).

2 Experimental Methods 80 rats (half male and half male) were selected according to animal weight gain, diet, and activity during the adaptation period to enter this experiment, and were divided into 4 groups by weight block grouping, with 20 rats in each group, half male and half male.

The concentrations of each component in a three-component drug were: HSYA 30 mg/ml, paeoniflorin 40 mg/ml, and albiflorin 4 mg/ml. The preparation method of a medicinal solution included: 3.0 g of the HSYA, 4.0 g of the paeoniflorin, and 0.4 g of the albiflorin were weighed with a precision balance (1/10000 g), and then dissolved in an appropriate amount of the normal saline (0.9% sodium chloride aqueous solution), diluted to 100 mL, sterilized and filtered to obtain a solution of the three-component drug.

The concentrations of each component in a seven-component drug were: HSYA 30 mg/ml, paeoniflorin 40 mg/ml, albiflorin 4 mg/ml, oxypaeoniflorin 4 mg/ml, senkyunolide I 4 mg/ml, SAAS 4 mg/ml, and ferulic acid 0.5 mg/ml. The preparation method of a medicinal solution included: 3.0 g of the HSYA, 4.0 g of the paeoniflorin, 0.4 g of the albiflorin, 0.4 g of oxypaeoniflorin, 0.4 g of senkyunolide I, 0.4 g of SAAS, and 0.05 g of ferulic acid were weighed, and then dissolved in an appropriate amount of the normal saline (0.9% sodium chloride aqueous solution), diluted to 100 mL, sterilized and filtered to obtain a solution of the seven-component drug.

An intravenous injection limit for rats was 6 mL/kg. In summary, a dosage of the three-component drug was: HSYA 180 mg/kg, paeoniflorin 240 mg/kg, albiflorin 24 mg/kg.

A dosage of the seven-component drug was: HSYA 180 mg/kg, paeoniflorin 240 mg/kg, albiflorin 24 mg/kg, oxypaeoniflorin 24 mg/kg, senkyunolide I 24 mg/kg, SAAS 24 mg/kg, and ferulic acid 3 mg/kg.

The rats in the experimental group were given a single dosage of 6 mL/kg of the three-component drug and the seven-component drug at the above concentrations, and injected slowly intravenously; while the rats in control group were given a same dosage of the normal saline.

After the administration, the rats were observed continuously for at least 2 h, and the observations were conducted once in the morning and afternoon on a 1st day after the administration and once a day thereafter, for a total of 14 days. During the observation period, the toxic reaction of the rats and the death of animals in each group were observed and recorded, and timely necropsy was conducted on dead or dying animals. 14 d after the administration, all surviving animals were autopsyed, and the main organs were observed with naked eyes for obvious abnormal changes; when changes in volume, color, and texture occurred in organs, these changes were recorded and histopathological examination should be conducted.

3. Experimental Results

Rats were given a single slow intravenous injection of the three-component drug. The results showed: (1) no abnormal symptoms were found in the animals after administration; (2) the body weight and weight growth rate of the animals in the administration group were not significantly different from those in the control group; (3) there was no obvious abnormality in the gross autopsy.

Rats were given a single slow intravenous injection of the seven-component drug. The results showed: (1) no abnormal symptoms were found in the animals after administration; (2) the body weight and weight growth rate of the animals in the administration group were not significantly different from those in the control group; (3) there was no obvious abnormality in the gross autopsy.

EXAMPLE 2

Evaluation of effects of the three-component drug and seven-component drug on the release of IL-6 from peritoneal macrophages of rats stimulated by LPS (Lipopolysaccharide)

1. Experimental Materials

Clean-grade male SD rats (180 g to 220 g), endotoxin (LPS), HSYA, paeoniflorin, albiflorin, oxypaeoniflorin, senkyunolide I, SAAS, ferulic acid, RPMI-1640) medium, 24-well plate, and IL-6 ELISA kit.

2 Experimental Methods

The peritoneal macrophages of male SD rats were isolated, including: the male SD rats were fasted for 12 h before operation, the abdominal cavity was opened after anesthesia, 10 mL of a pre-cooled PBS solution was injected into the abdominal cavity, and the abdominal wall was lightly pressed and kneaded with fingers to make the fluid flow in the abdominal cavity. The fluid in the abdominal cavity was aspirated and injected into a sterilized tube, and then the abdominal cavity was lavaged once with 10 mL of the pre-cooled PBS solution using the method as the same above. The collected lavage fluid was combined, centrifuged at 250 g, 4° C. for 10 min, and a supernatant was discarded. 2 mL of an erythrocyte lysate was added to lyse the erythrocytes, oscillation was conducted gently twice, 5 sec each time, allowed to stand for 5 min, and 4 mL of a D-Hanks solution was added to terminate the lysis. Centrifugation was conducted for a second time as above and a supernatant was discarded. A resulting cell pellet was washed with a culture medium, and then resuspended to obtain a cell suspension of $2\times10^6$/mL. The cell suspension was inoculated in the 24-well plate and then cultured in a cell incubator with 5% $CO_2$ at 37° C. Each group had 6 parallel wells. After culturing for 12 h and 24 h, a supernatant was collected separately, and a content of cytokines was determined by a double-antibody one-step sandwich method and enzyme-linked immunosorbent assay (ELISA).

The supernatant for experiment was divided into a control group, a model group, and a drug treatment group. The treatment methods of each group were as follows: the cells of each group were cultured overnight in a cell incubator at 37° C. with 5% $CO_2$. The corresponding volume of a culture solution was added to the control group and the model group, and the same volume of the corresponding concentration of a drug solution was added to the drug treatment group, and each group was incubated in the incubator for 1 h. LPS was not added to the control group, while the LPS (75 ng/mL) was added to the model group and drug treatment group. After 12 h and 24 h, 0.5 mL of an obtained cell culture supernatant was collected from each group, stored in a −20° C. refrigerator, and concentrated for the detection of corresponding cytokines. The drug treatment group was subjected to an orthogonal experiment, and a grouping method of the orthogonal experiment was shown in Table 1 and Table 2.

TABLE 1

Orthogonal experimental grouping of three-component drug groups

| Group | HSYA | Paeoniflorin | Albiflorin |
|---|---|---|---|
| 1 | Low | Low | Low |
| 2 | Low | Moderate | High |
| 3 | Low | High | Moderate |
| 4 | Moderate | Low | High |
| 5 | Moderate | Moderate | Moderate |
| 6 | Moderate | High | Low |
| 7 | High | Low | Moderate |
| 8 | High | Moderate | Low |
| 9 | High | High | High |

In Table 1, the three concentrations of HSYA were low (2 μM), moderate (20 μM), and high (200 μM). The three concentrations of paeoniflorin were low (4 μM), moderate (40 μM), and high (400 μM). The three concentrations of albiflorin were low (2 μM), moderate (20 μM, and high (200 μM). The three concentrations of oxypaeoniflorin were low (2 μM), moderate (20 μM, and high (200 μM). The three concentrations of senkyunolide I were low (4 μM), moderate (40 μM), and high (400 μM). The three concentrations of SAAS were low (2 μM), moderate (20 μM), and high (200 μM). The three concentrations of ferulic acid were low (4 μM), moderate (40 μM, and high (400 μM).

TABLE 2

Orthogonal experimental grouping of seven-component drug groups

| Group | HSYA | Paeoniflorin | Albiflorin | Oxypaeoniflorin | Senkyunolide I | SAAS | Ferulic acid |
|---|---|---|---|---|---|---|---|
| 1 | Low | Low | Low | Low | Low | Low | Low |
| 2 | Low | Moderate | Moderate | Moderate | Moderate | Moderate | Moderate |
| 3 | Low | High | High | High | High | High | High |
| 4 | Moderate | Low | Low | Moderate | Moderate | High | High |
| 5 | Moderate | Moderate | Moderate | High | High | Low | Low |
| 6 | Moderate | High | High | Low | Low | Moderate | Moderate |
| 7 | High | Low | Moderate | Low | High | Moderate | High |
| 8 | High | Moderate | High | Moderate | Low | High | Low |

TABLE 2-continued

| Orthogonal experimental grouping of seven-component drug groups | | | | | | | |
|---|---|---|---|---|---|---|---|
| Group | HSYA | Paeoniflorin | Albiflorin | Oxypaeoniflorin | Senkyunolide I | SAAS | Ferulic acid |
| 9 | High | High | Low | High | Moderate | Low | Moderate |
| 10 | Low | Low | High | High | Moderate | Moderate | Low |
| 11 | Low | Moderate | Low | Low | High | High | Moderate |
| 12 | Low | High | Moderate | Moderate | Low | Low | High |
| 13 | Moderate | Low | Moderate | High | Low | High | Moderate |
| 14 | Moderate | Moderate | High | Low | Moderate | Low | High |
| 15 | Moderate | High | Low | Moderate | High | Moderate | Low |
| 16 | High | Low | High | Moderate | High | Low | Moderate |
| 17 | High | Moderate | Low | High | Low | Moderate | High |
| 18 | High | High | Moderate | Low | Moderate | High | Low |

A preparation method of medical solution was as follows: according to the corresponding concentration of each group in Table 1, the appropriate weight of HSYA, paeoniflorin, and albiflorin were weighed with a precision balance (1/10000 g), combined into different volumetric flasks according to the combinations of different concentrations, and then dissolved in appropriate medium (containing 10% fetal bovine serum), respectively, to obtain 9 groups of three-component drugs with corresponding concentrations.

According to the corresponding concentration of each group in Table 2, the appropriate weight of HSYA, paeoniflorin, albiflorin, oxypaeoniflorin, senkyunolide I, SAAS, and ferulic acid were weighed with a precision balance (1/10000 g), combined into different volumetric flasks according to the combinations of different concentrations, and then dissolved in appropriate medium (containing 10% fetal bovine serum), respectively, to obtain 18 groups of seven-component drugs with corresponding concentrations.

3. Experimental Results

The experimental results (Table 3) showed that compared with the model group, the three-component drug and the seven-component drug in each dosage group could significantly reduce the release level of IL-6 in rat peritoneal macrophages at 12 h and 24 h. This indicated that the three-component drug and the seven-component drug both had a desirable inhibitory effect on the early inflammatory factors of the cell model of sepsis.

TABLE 3

| Effects of three-component drug group and seven-component drug group on expression of IL-6 in rat peritoneal macrophages stimulated by LPS (x ± s, n = 6, unit: pg/mL) | | | |
|---|---|---|---|
| Group | | 12 h | 24 h |
| Control group | | 113.91 ± 5.75* | 113.91 ± 5.75* |
| Model group | | 223.35 ± 6.18 | 242.15 ± 2.83 |
| Three-component drug group | 1 | 178.94 ± 3.54* | 186.97 ± 2.34* |
| | 2 | 168.63 ± 2.10* | 180.28 ± 1.55* |
| | 3 | 172.05 ± 1.99* | 183.26 ± 1.61* |
| | 4 | 170.63 ± 2.69* | 181.37 ± 2.17* |
| | 5 | 172.50 ± 3.95* | 181.67 ± 2.31* |
| | 6 | 168.36 ± 3.21* | 182.51 ± 2.54* |
| | 7 | 170.67 ± 3.54* | 180.12 ± 2.40* |
| | 8 | 169.36 ± 4.16* | 182.48 ± 3.16* |
| | 9 | 162.78 ± 2.05* | 172.39 ± 2.75* |
| Seven-component drug group | 1 | 146.73 ± 1.51* | 167.26 ± 1.47* |
| | 2 | 140.88 ± 2.49* | 163.92 ± 2.17* |
| | 3 | 139.60 ± 2.52* | 160.90 ± 3.51* |
| | 4 | 139.70 ± 2.52* | 164.94 ± 0.94* |
| | 5 | 142.20 ± 3.19* | 162.57 ± 3.61* |
| | 6 | 140.90 ± 2.52* | 163.42 ± 2.49* |

TABLE 3-continued

| Effects of three-component drug group and seven-component drug group on expression of IL-6 in rat peritoneal macrophages stimulated by LPS (x ± s, n = 6, unit: pg/mL) | | | |
|---|---|---|---|
| Group | | 12 h | 24 h |
| | 7 | 141.59 ± 3.43* | 161.39 ± 2.09* |
| | 8 | 141.15 ± 2.30* | 161.30 ± 2.41* |
| | 9 | 138.76 ± 3.58* | 158.96 ± 1.82* |
| | 10 | 142.13 ± 2.54* | 160.73 ± 3.98* |
| | 11 | 140.92 ± 3.12* | 163.03 ± 3.52* |
| | 12 | 140.36 ± 2.89* | 161.37 ± 2.90* |
| | 13 | 142.99 ± 3.67* | 163.87 ± 2.60* |
| | 14 | 142.20 ± 2.44* | 162.58 ± 2.78* |
| | 15 | 139.67 ± 2.04* | 161.68 ± 1.95* |
| | 16 | 139.65 ± 2.86* | 163.63 ± 3.52* |
| | 17 | 141.86 ± 1.84* | 161.94 ± 1.69* |
| | 18 | 134.86 ± 1.01* | 155.36 ± 3.40* |

Note:
*indicated $P < 0.05$ when compared with the model group.

EXAMPLE 3

Evaluation of effects of the three-component drug and seven-component drug on the release of HMGB1 from peritoneal macrophages of rats stimulated by LPS 1. Experimental Materials Clean-grade male SD rats (180 g to 220 g), endotoxin (LPS), HSYA, paeoniflorin, albiflorin, oxypaeoniflorin, senkyunolide I, SAAS, ferulic acid, RPMI-1640 medium, 24-well plate, and HMGB1 ELISA kit.

2 Experimental Methods

The peritoneal macrophages of male SD rats were isolated, including: the male SD rats were fasted for 12 h before operation, the abdominal cavity was opened after anesthesia, 10 mL of a pre-cooled PBS solution was injected into the abdominal cavity, and the abdominal wall was lightly pressed and kneaded with fingers to make the fluid flow in the abdominal cavity. The fluid in the abdominal cavity was aspirated and injected into a sterilized tube, and then the abdominal cavity was lavaged once with 10 mL of the pre-cooled PBS solution using the method as the same above. The collected lavage fluid was combined, centrifuged at 250 g, 4° C. for 10 min, and a supernatant was discarded. 2 mL of erythrocyte lysate was added to lyse the erythrocytes, oscillation was conducted gently twice, 5 sec each time, allowed to stand for 5 min, and 4 mL of a D-Hanks solution was added to terminate the lysis. Centrifugation was conducted for a second time as above and a supernatant was discarded. A resulting cell pellet was washed with a culture medium, and then resuspended to obtain a cell suspension of $2\times10^6$/mL. The prepared cell suspension was inoculated in the 24-well plate and then cultured in a cell incubator with 5% $CO_2$ at 37° C. Each group had 6 parallel wells. After culturing for 48 h and 72 h, a supernatant was collected separately, and a content of cytokines was determined by a double-antibody one-step sandwich method and enzyme-linked immunosorbent assay (ELISA).

The supernatants for experiment were divided into a control group, a model group, and a drug treatment group. The treatment methods of each group were as follows: the cells of each group were cultured overnight in a cell incubator at 37° C. with 5% $CO_2$. The corresponding volume of a culture solution was added to the control group and the model group, and the same volume of the corresponding concentration of a medical solution was added to the drug treatment group, and each group was incubated in the incubator for 1 h. LPS was not added to the control group, while the LPS (75 ng/mL) was added to the model group and drug treatment group. After 48 h and 72 h, 0.5 mL of obtained cell culture supernatant was collected from each group, stored in a −20° C. refrigerator, and concentrated for the detection of corresponding cytokines. The experimental grouping and the preparation method of the medical solution were the same as those in Example 2.

3. Experimental Results

The experimental results (Table 4) showed that compared with the model group, the three-component drug and the seven-component drug in each dosage group could significantly reduce the release level of HMGB1 in rat peritoneal macrophages 48 h and 72 h. This indicated that the three-component drug and the seven-component drug both had a desirable inhibitory effect on the late inflammatory factors of the cell model of sepsis.

TABLE 4

Effects of three-component drug group and seven-component drug group on expression of HMGB1 in rat peritoneal macrophages stimulated by LPS (x ± s, n = 6, unit: pg/mL)

| Group | | 48 h | 72 h |
|---|---|---|---|
| Control group | | 24.96 ± 1.95* | 24.89 ± 1.84* |
| Model group | | 54.26 ± 2.66 | 73.76 ± 2.73 |
| Three-component drug group | 1 | 43.37 ± 1.34* | 60.92 ± 2.75* |
| | 2 | 38.59 ± 3.30* | 55.68 ± 1.78* |
| | 3 | 36.79 ± 3.16* | 55.69 ± 3.04* |
| | 4 | 36.09 ± 3.71* | 55.51 ± 2.20* |
| | 5 | 36.71 ± 3.38* | 54.18 ± 2.25* |
| | 6 | 36.40 ± 3.38* | 55.95 ± 2.06* |
| | 7 | 35.08 ± 2.72* | 54.62 ± 2.45* |
| | 8 | 39.71 ± 2.98* | 54.44 ± 2.42* |
| | 9 | 30.46 ± 1.81* | 47.51 ± 2.55* |
| Seven-component drug group | 1 | 39.93 ± 1.45* | 48.87 ± 1.20* |
| | 2 | 34.38 ± 2.66* | 41.71 ± 1.40* |
| | 3 | 35.26 ± 2.35* | 43.80 ± 2.38* |
| | 4 | 33.88 ± 2.42* | 43.55 ± 2.09* |
| | 5 | 35.43 ± 2.27* | 42.76 ± 2.20* |
| | 6 | 33.45 ± 2.32* | 42.93 ± 2.01* |
| | 7 | 34.74 ± 2.28* | 43.24 ± 3.25* |
| | 8 | 35.84 ± 2.81* | 43.32 ± 2.28* |
| | 9 | 34.88 ± 1.80* | 44.35 ± 2.51* |
| | 10 | 35.65 ± 2.53* | 42.45 ± 1.76* |
| | 11 | 34.58 ± 2.15* | 43.50 ± 2.87* |
| | 12 | 36.50 ± 1.54* | 44.40 ± 3.63* |
| | 13 | 33.55 ± 0.71* | 43.24 ± 2.89* |
| | 14 | 35.34 ± 2.22* | 44.68 ± 2.61* |

TABLE 4-continued

Effects of three-component drug group and seven-component drug group on expression of HMGB1 in rat peritoneal macrophages stimulated by LPS (x ± s, n = 6, unit: pg/mL)

| Group | | 48 h | 72 h |
|---|---|---|---|
| | 15 | 34.91 ± 2.19* | 44.64 ± 2.82* |
| | 16 | 36.56 ± 1.56* | 42.64 ± 2.30* |
| | 17 | 33.01 ± 1.49* | 43.52 ± 2.47* |
| | 18 | 29.43 ± 1.05* | 37.16 ± 1.23* |

Note:
*indicated $P < 0.05$ when compared with the model group.

EXAMPLE 4

Evaluation of effects of the three-component drug and seven-component drug on the release of TM from abdominal aortic endothelial cells of rats stimulated by LPS

1. Experimental Materials

Clean-grade male SD rats (180 g to 220 g), LPS, HSYA, paeoniflorin, albiflorin, oxypaeoniflorin, senkyunolide I, SAAS, ferulic acid, ECM medium, 24-well plate, and thrombomodulin (TM) ELISA Kit.

2 Experimental Methods

Rats were killed by cervical dislocation and soaked in 75% ethanol for 5 min. The thoracic and abdominal cavities were opened layer by layer, the thoracic and abdominal aorta was fully exposed, and the surrounding tissues were separated. The aorta was separated from a proximal end to the branch of common iliac artery, and placed in a petri dish containing PBS. The adipose and fibrous tissues of the vascular adventitia were aseptically stripped, and the vascular lumen was flushed with PBS. The aorta was cut into small pieces of about 1.5 mm×1.5 mm, placed in 6 mL of 0.25% type IV collagenase, digested at 37° C. for 15 min, and shaken every 5 min. The digested juice was carefully aspirated, tissue blocks were retained, then 6 mL of 1.0% dispase was added to digest at 37° C. for 15 min, and shaken every 5 min. The digestive juice was aspirated, 10 mL of ECM was added, pipetted repeatedly, and centrifuged at 1,000 r/min for 10 min. The medium and digested juice was discarded and the fragments were retained. The tissue blocks were spread on the bottom of a 10 cm petri dish, placed upside down in an oven at 37° C. for 2 h to make the tissue blocks stick firmly, an appropriate amount of ECM was added to submerge the tissue blocks. The tissue blocks were cultured at 37° C. in a $CO_2$-saturated humidity incubator with a volume fraction of 5%, and the medium was replaced every 3 d. After about 7 d, it was seen that endothelial cells spread outward from the edge of the tissue block and gradually extended outward, showing a flat short spindle or polygonal shape. The tissue blocks were removed, the endothelial cells were digested with 0.25% trypsin, and passaged in a 25 $cm^2$ culture flask at a ratio of 1:3, and the experiments were conducted with the 3rd- to 4th-generation cells.

The endothelial cells were cultured according to the above-mentioned method for culturing rat abdominal aortic endothelial cells to prepare a cell suspension. The cell suspension was inoculated in a 24-well plate at $1.2\times10^5$/mL and cultured at 37° C. About 12 h later, the model group and the drug treatment group were stimulated with LPS; and 1 h later, each group was given different medicinal solutions for intervention. The supernatants were collected at 24 h, 48 h, and 72 h after the stimulation, respectively.

The experiment was divided into a control group, a model group, and a drug treatment group. The treatment methods of each group were as follows: the cells of each group were cultured overnight in a cell incubator at 37° C. with 5% $CO_2$. The corresponding volume of a culture solution was added to the control group and the model group, and the same volume of the corresponding concentration of a medical solution was added to the drug treatment group, and each group was incubated in the incubator for 1 h. LPS was not added to the control group, while the LPS (75 ng/mL) was added to the model group and drug treatment group. After 24 h, 48 h, and 72 h, 0.5 mL of an obtained cell culture supernatant was collected from each group, stored in a −20° C. refrigerator, and concentrated for the detection of corresponding cytokines. The experimental grouping and the preparation method of the medical solution were the same as those in Example 2.

3. Experimental Results

TM is ubiquitously present on the surface of rat abdominal aortic endothelial cells, and plays an anticoagulant effect by binding to thrombin and activating the protein C system. In the state of sepsis, TM is released into the surrounding blood in large quantities, thereby weakening the anticoagulant effect. Under drug intervention, the reduction of TM contributes to the balance of anticoagulant/procoagulant for coagulation factors, and is conducive to promoting the recovery of the coagulation function of cells/body to a normal state.

The experimental results (Table 5) showed that compared with the model group, the three-component drug and seven-component drug in each concentration group could reduce the release of TM in rat abdominal aortic endothelial cells at 24 h, 48 h, and 72 h. This indicated that the three-component drug and the seven-component drug have the effect of promoting the normalization of coagulation function on the sepsis cell model.

TABLE 5

Effects of three-component drug group and seven-component drug group on TM release in rat abdominal aortic endothelial cells stimulated by LPS (x ± s, n = 6, unit: pg/mL)

| Group | | 24 h | 48 h | 72 h |
|---|---|---|---|---|
| Control group | | 8.34 ± 0.87* | 8.99 ± 1.03* | 8.63 ± 0.96* |
| Model group | | 40.92 ± 1.55 | 59.90 ± 2.47 | 49.31 ± 1.54 |
| Three-component drug group | 1 | 27.19 ± 0.86* | 38.00 ± 1.56* | 46.57 ± 1.57* |
| | 2 | 21.34 ± 2.39* | 32.52 ± 2.20* | 42.48 ± 1.45* |
| | 3 | 23.09 ± 1.76* | 33.24 ± 2.64* | 41.36 ± 2.13* |
| | 4 | 21.44 ± 2.88* | 33.52 ± 1.66* | 41.04 ± 1.82* |
| | 5 | 20.87 ± 2.15* | 33.18 ± 2.62* | 40.83 ± 2.83* |
| | 6 | 18.86 ± 1.90* | 32.90 ± 2.67* | 41.33 ± 2.07* |
| | 7 | 21.37 ± 2.54* | 33.81 ± 3.19* | 40.22 ± 2.13* |
| | 8 | 22.37 ± 2.24* | 33.08 ± 3.12* | 41.79 ± 2.02* |
| | 9 | 16.69 ± 1.36* | 27.57 ± 1.84* | 35.95 ± 1.94* |
| Seven-component drug group | 1 | 23.61 ± 1.14* | 33.69 ± 2.20* | 41.16 ± 1.47* |
| | 2 | 19.29 ± 2.20* | 29.56 ± 0.87* | 35.43 ± 2.67* |
| | 3 | 18.33 ± 2.67* | 27.72 ± 2.71* | 33.94 ± 1.69* |
| | 4 | 21.22 ± 2.09* | 27.76 ± 2.66* | 35.07 ± 2.31* |
| | 5 | 18.17 ± 1.98* | 28.01 ± 2.78* | 36.40 ± 2.89* |
| | 6 | 20.53 ± 1.70* | 28.40 ± 3.26* | 35.21 ± 3.34* |
| | 7 | 17.32 ± 1.08* | 29.17 ± 3.62* | 34.79 ± 2.27* |
| | 8 | 19.22 ± 2.35* | 28.48 ± 3.60* | 36.15 ± 3.03* |
| | 9 | 18.05 ± 1.93* | 28.83 ± 1.82* | 36.57 ± 2.31* |
| | 10 | 19.38 ± 2.97* | 29.19 ± 1.66* | 35.60 ± 2.67* |

TABLE 5-continued

Effects of three-component drug group and seven-component drug group on TM release in rat abdominal aortic endothelial cells stimulated by LPS (x ± s, n = 6, unit: pg/mL)

| Group | | 24 h | 48 h | 72 h |
|---|---|---|---|---|
| | 11 | 18.69 ± 2.68* | 35.88 ± 2.40* | 33.82 ± 2.83* |
| | 12 | 19.43 ± 3.20* | 28.70 ± 2.98* | 34.55 ± 3.48* |
| | 13 | 19.12 ± 1.92* | 27.79 ± 3.07* | 36.76 ± 2.13* |
| | 14 | 18.54 ± 2.69* | 27.47 ± 2.43* | 34.72 ± 3.00* |
| | 15 | 19.09 ± 2.55* | 27.74 ± 3.85* | 34.16 ± 3.28* |
| | 16 | 18.36 ± 1.61* | 28.04 ± 2.39* | 37.39 ± 2.39* |
| | 17 | 18.73 ± 2.73* | 28.83 ± 3.11* | 35.15 ± 3.38* |
| | 18 | 13.13 ± 1.63* | 22.57 ± 1.27* | 30.62 ± 0.98* |

Note:
*indicated $P < 0.05$ when compared with the model group.

EXAMPLE 5

Evaluation of effects of the three-component drug and seven-component drug on the release of TF from abdominal aortic endothelial cells of rats stimulated by LPS

1. Experimental Materials

Clean-grade male SD rats (180 g to 220 g), LPS, HSYA, paeoniflorin, albiflorin, oxypaeoniflorin, senkyunolide I, SAAS, ferulic acid, ECM medium, 24-well plate, and tissue factor (TF) ELISA Kit.

2. Experimental Methods

The experimental method and the grouping and treatment methods were the same as those in Example 4.

The experimental grouping and the preparation method of the medical solution were the same as those in Example 2.

3. Experimental Results

TF is an important procoagulant factor in rat abdominal aortic endothelial cells. In the state of sepsis, a hypercoagulable state is manifested by the massive release of TF. Under drug intervention, the reduction of TF contributes to the balance of anticoagulant/procoagulant for coagulation factors, and is conducive to promoting the recovery of the coagulation function of cells/body to a normal state.

The experimental results (Table 6) showed that compared with the model group, the three-component drug and seven-component drug in each concentration group could reduce the release of procoagulant factors TF in rat abdominal aortic endothelial cells at 24 h, 48 h, and 72 h. This indicated that the three-component drug and the seven-component drug have the effect of promoting the normalization of coagulation function on the sepsis cell model.

TABLE 6

Effects of three-component drug group and seven-component drug group on TF release in rat abdominal aortic endothelial cells stimulated by LPS (x ± s, n = 6, unit: pg/mL)

| Group | | 24 h | 48 h | 72 h |
|---|---|---|---|---|
| Control group | | 18.54 ± 0.98* | 19.02 ± 0.83* | 16.73 ± 1.19* |
| Model group | | 32.39 ± 0.73 | 33.49 ± 1.79 | 28.99 ± 0.70 |
| Three-component drug group | 1 | 26.66 ± 0.66* | 27.07 ± 1.22* | 25.21 ± 1.13* |
| | 2 | 23.91 ± 0.82* | 24.00 ± 0.79* | 23.27 ± 0.93* |
| | 3 | 23.70 ± 1.10* | 22.45 ± 1.16* | 23.92 ± 1.05* |
| | 4 | 23.78 ± 0.46* | 21.31 ± 1.16* | 23.72 ± 0.87* |
| | 5 | 22.54 ± 0.98* | 21.66 ± 1.57* | 23.09 ± 0.81* |

TABLE 6-continued

Effects of three-component drug group and seven-component drug group on TF release in rat abdominal aortic endothelial cells stimulated by LPS (x ± s, n = 6, unit: pg/mL)

| Group | | 24 h | 48 h | 72 h |
|---|---|---|---|---|
| | 6 | 22.32 ± 1.55* | 21.55 ± 1.31* | 23.91 ± 1.08* |
| | 7 | 20.92 ± 0.82* | 21.45 ± 1.45* | 22.63 ± 1.02* |
| | 8 | 20.54 ± 1.88* | 20.91 ± 0.62* | 20.30 ± 0.97* |
| | 9 | 20.12 ± 0.96* | 19.27 ± 0.67* | 19.16 ± 0.73* |
| Seven-component drug group | 1 | 24.68 ± 0.87* | 25.07 ± 0.71* | 22.21 ± 0.65* |
| | 2 | 21.86 ± 1.70* | 25.75 ± 0.45* | 22.11 ± 0.47* |
| | 3 | 21.08 ± 0.84* | 23.03 ± 0.57* | 21.89 ± 0.71* |
| | 4 | 20.81 ± 1.81* | 21.76 ± 0.89* | 21.74 ± 0.98* |
| | 5 | 21.72 ± 1.43* | 24.86 ± 0.65* | 20.68 ± 0.76* |
| | 6 | 21.56 ± 1.40* | 22.10 ± 0.41* | 20.72 ± 1.00* |
| | 7 | 21.04 ± 1.43* | 22.16 ± 0.65* | 20.70 ± 0.99* |
| | 8 | 22.37 ± 0.98* | 21.34 ± 0.85* | 20.39 ± 1.42* |
| | 9 | 21.62 ± 2.16* | 20.89 ± 0.76* | 19.99 ± 1.29* |
| | 10 | 22.21 ± 0.71* | 20.74 ± 1.01* | 18.72 ± 0.90* |
| | 11 | 21.08 ± 1.40* | 20.57 ± 0.86* | 20.21 ± 1.34* |
| | 12 | 21.63 ± 2.04* | 20.77 ± 1.38* | 19.85 ± 0.91* |
| | 13 | 21.73 ± 1.69* | 20.95 ± 1.25* | 19.54 ± 1.16* |
| | 14 | 21.91 ± 0.99* | 19.79 ± 1.04* | 19.03 ± 0.86* |
| | 15 | 20.52 ± 0.95* | 20.76 ± 1.47* | 19.44 ± 0.77* |
| | 16 | 22.01 ± 1.64* | 20.51 ± 1.16* | 18.63 ± 0.98* |
| | 17 | 20.63 ± 0.74* | 19.46 ± 0.76* | 18.98 ± 0.91* |
| | 18 | 19.12 ± 0.76* | 19.44 ± 0.83* | 17.30 ± 0.96* |

Note:
*indicated $P < 0.05$ when compared with the model group.

EXAMPLE 6

Evaluation of effects of the three-component drug and seven-component drug on the apoptosis of spleen regulatory T cells (Tregs) of rats stimulated by LPS

1. Experimental Materials

Clean-grade male SD rats (180 g to 220 g), LPS, HSYA, paeoniflorin, albiflorin, oxypaeoniflorin, senkyunolide I, SAAS, ferulic acid, 1640 medium, 24-well plate, phycoerythrin (PE)-anti-rat CD25, fluorescein isothiocyanate (FITC)-labeled anti-rat CD4, and fluorescein isothiocyanate (FITC)-labeled annexin V apoptosis kit; rat CD25-APC antibody kit, APC magnetic beads, CD4 magnetic beads, MACS Buffer, MiniMACS magnetic separator, and separation column (LS); anti-rat CD3 monoclonal antibody, anti-rat CD28 monoclonal antibody.

2 Experimental Methods

The male SD rats were killed by neck dislocation, and the spleens were taken. The spleen was ground with a plunger of a sterile syringe, a resulting suspension was pipetted into a centrifuge tube, centrifuged at 1,200 rpm for 7 min, and a supernatant was discarded. An appropriate amount of the MACS Buffer (10 mL/spleen) was added to resuspend. A resuspended product was added to an upper layer of a lymphocyte separation medium (1:1) along the tube wall, and centrifuged at 3,000 rpm for 15 min. An obtained middle-layer liquid was aspirated with a straw, put into another centrifuge tube, a cleaning solution was added, centrifugation was conducted at 1,200 rpm for 7 min, and a supernatant was discarded. The MACS Buffer was added to resuspend for later use.

1 μL of the anti-CD25-APC antibody was added into per $1\times10^7$ monocytes, incubated at 4° C. for 15 min, and washed with the MACS Buffer. 20 μL of the anti-APC magnetic beads and 80 μL of the MACS Buffer were added into per $1\times10^7$ cells, incubated at 4° C. for 15 min, washed with the MACS Buffer, and resuspended with an appropriate amount of the MACS Buffer, and CD25+ cells were obtained by magnetic separation on the LS column.

After the CD25+ cells were counted, 20 μL of a dissociation agent was added to per $1\times10^7$ cells, incubated at 4° C. for 1 min, and washed with the MACS Buffer. 20 μL of the anti-CD4 magnetic beads and 30 μL of a terminator were added into per $1\times10^7$ cells, incubated at 4° C. for 15 min, and washed with the MACS Buffer. An appropriate amount of the MACS Buffer was added to resuspend, and magnetic separation was conducted on an LS column to obtain CD4+ CD25+ cells.

The Tregs were resuspended with an appropriate amount of culture medium, and the cell number was adjusted to $2.5\times10^6$/mL. 100 μL of cells were inoculated into each well of a 96-well plate. The model group and the experimental group were stimulated by adding CD3/CD28 (0.5 μg/$10^6$ for CD3 and 1 μg/$10^6$ for CD28)+LPS (1 μg/mL). The experiment was divided into control group, model group, and drug treatment group. 1 h later, the model group and the drug treatment group were intervened with different medicinal solutions, and incubated in a $CO_2$ incubator at 37° C. for 72 h.

The cells were collected, washed with pre-cooled PBS, and washed with 1 ml of a 1×Binding Buffer, centrifuged, and a supernatant was removed. 5 μL of the FITC Annexin V and 5 μL of PI were added to the remaining 100 μL of cells, and incubated at room temperature (25° C.) in the dark for 15 min. 200 μL of the 1×Binding Buffer was added into the cells, mixed well, and detected by flow cytometer within 1 h.

The grouping and treatments were as follows: model group: the cells were cultured overnight in a cell incubator, and then stimulated by adding LPS (75 ng/ml). Drug treatment group: the cells were incubated with medicinal solutions at corresponding concentrations for 1 h, and then stimulated with LPS. After 72 h of intervention in the experimental groups with different concentrations, 0.5 mL of a supernatant of a cell culture medium was collected and stored in a −20° C. refrigerator, and corresponding cytokines were detected centrally.

The experimental grouping and the preparation method of the medical solution were the same as those in Example 2.

3. Experimental Results

After the function was enhanced, the Tregs inhibited ordinary T cells by producing immunosuppressive factors such as IL-10, IL-35, and TGF-β, and killed target cells by granzyme B and perforin-1, thereby exerting an immunosuppressive effect. The Tregs could also induce DC dendritic cells to produce indoleamine 2,3-dioxygenase, which catalyzed the decomposition of tryptophan into kynurenin, resulting in the death of surrounding cells. The Tregs could also induce DC cells to secrete other amino acid-related enzymes, thereby inhibiting the proliferation of effector T cells and exerting an immunosuppressive effect. Therefore, drugs could promote the apoptosis of Treg cells in a certain period of time, and played a highly important role in the immune regulation of the body. Compared with the model group, the three-component drug and the seven-component drug in each dose group could promote the apoptosis of regulatory T cells (Tregs) in rats (Table 7).

TABLE 7

Effects of three-component drug group and seven-component drug group on apoptosis of rat spleen regulatory T cells stimulated by LPS (x ± s, n = 6, unit: %)

| Group | | 72 h |
|---|---|---|
| Control group | | 32.20 ± 3.23* |
| Model group | | 16.46 ± 1.94 |
| Three-component drug group | 1 | 18.36 ± 1.70* |
| | 2 | 22.55 ± 1.11* |
| | 3 | 22.55 ± 1.59* |
| | 4 | 23.30 ± 0.57* |
| | 5 | 26.00 ± 0.91* |
| | 6 | 26.28 ± 0.96* |
| | 7 | 26.55 ± 0.81* |
| | 8 | 28.51 ± 1.48* |
| | 9 | 29.06 ± 0.91* |
| Seven-component drug group | 1 | 20.73 ± 1.07* |
| | 2 | 23.66 ± 0.74* |
| | 3 | 24.95 ± 0.82* |
| | 4 | 24.71 ± 0.86* |
| | 5 | 24.78 ± 1.33* |
| | 6 | 24.40 ± 0.81* |
| | 7 | 25.88 ± 1.18* |
| | 8 | 25.25 ± 1.76* |
| | 9 | 24.78 ± 1.11* |
| | 10 | 24.85 ± 1.36* |
| | 11 | 26.33 ± 0.95* |
| | 12 | 25.85 ± 1.39* |
| | 13 | 27.32 ± 1.44* |
| | 14 | 26.63 ± 1.83* |
| | 15 | 26.62 ± 0.75* |
| | 16 | 28.55 ± 0.74* |
| | 17 | 30.54 ± 1.15* |
| | 18 | 30.76 ± 0.90* |

Note:
*indicated $P < 0.05$ when compared with the model group.

EXAMPLE 7

Effects of three-component drug and seven-component drug on the expression of CTLA-4 and Foxp3 in spleen regulatory T cells of rats stimulated by LPS

1. Experimental Materials

Clean-grade male SD rats (180 g to 220 g), LPS, HSYA, paeoniflorin, albiflorin, oxypaeoniflorin, senkyunolide I, SAAS, ferulic acid, 1640 medium, 24-well plate, phycoerythrin (PE)-anti-rat CD25, and fluorescein isothiocyanate (FITC)-labeled anti-rat CD4; rat anti-PE kit, CD4 magnetic beads, MiniMACS magnetic separation instrument, and separation column: PE-labeled Foxp3 kit, PE-labeled CTLA-4 kit, anti-rat CD3 monoclonal antibody, and anti-rat CD28 monoclonal antibody.

2 Experimental Methods

The experimental method and the grouping and treatment methods were the same as those in Example 6.

The experimental grouping and the preparation method of the medical solution were the same as those in Example 2.

3. Experimental Results

The Foxp3 Tregs inhibited ordinary T cells by producing immunosuppressive factors such as IL-10, IL-35, and TGF-β, and killed target cells by granzyme B and perforin-1, thereby exerting an immunosuppressive effect. CTLA-4 could also induce DC dendritic cells to produce indoleamine 2,3-dioxygenase, which catalyzed the decomposition of tryptophan into kynurenin, resulting in the death of surrounding cells. This factor could also induce DC cells to secrete other amino acid-related enzymes, thereby inhibiting the proliferation of effector T cells and exerting an immunosuppressive effect. Therefore, Tregs played a highly important role in immune regulation through Foxp3 and CTLA-4, and the expression of Foxp3 was closely related to the function of regulatory T cells (Tregs).

Compared with the model group, the three-component drug and the seven-component drug in each dosage group could reduce the expression levels of CTLA-4 and Foxp3 in rat regulatory T cells (Tregs) at 72 h. This indicated that the three-component drug and the seven-component drug could reduce the expression levels of CTLA-4 and Foxp3 in regulatory T cells (Tregs) of rats with sepsis at 72 h (Table 8 and Table 9).

TABLE 8

Effects of three-component drug group and seven-component drug group on expression of CTLA-4 in spleen regulatory T cells of rats stimulated by LPS (x ± s, n = 6, unit: %)

| Group | | 72 h |
|---|---|---|
| Control group | | 23.09 ± 2.09* |
| Model group | | 43.53 ± 3.46 |
| Three-component drug group | 1 | 37.46 ± 1.48* |
| | 2 | 34.60 ± 0.98* |
| | 3 | 33.81 ± 0.73* |
| | 4 | 35.07 ± 0.86* |
| | 5 | 32.66 ± 1.49* |
| | 6 | 32.13 ± 1.14* |
| | 7 | 30.29 ± 1.49* |
| | 8 | 25.06 ± 0.82* |
| | 9 | 25.87 ± 1.07* |
| Seven-component drug group | 1 | 33.65 ± 1.58* |
| | 2 | 34.93 ± 0.73* |
| | 3 | 33.94 ± 1.36* |
| | 4 | 32.01 ± 1.35* |
| | 5 | 31.81 ± 1.55* |
| | 6 | 31.73 ± 1.09* |
| | 7 | 30.17 ± 1.03* |
| | 8 | 31.25 ± 1.30* |
| | 9 | 31.45 ± 0.93* |
| | 10 | 32.04 ± 1.17* |
| | 11 | 28.60 ± 0.76* |
| | 12 | 27.85 ± 0.79* |
| | 13 | 28.08 ± 1.05* |
| | 14 | 28.02 ± 0.51* |
| | 15 | 27.57 ± 1.05* |
| | 16 | 24.02 ± 0.90* |
| | 17 | 24.25 ± 1.33* |
| | 18 | 24.74 ± 1.22* |

Note:
*indicated $P < 0.05$ when compared with the model group.

TABLE 9

Effects of three-component drug group and seven-component drug group on expression of Foxp3 in spleen regulatory T cells of rats stimulated by LPS (x ± s, n = 6, unit: %)

| Group | | 72 h |
|---|---|---|
| Control group | | 51.60 ± 3.52* |
| Model group | | 78.99 ± 2.79 |
| Three-component drug group | 1 | 71.41 ± 2.71* |
| | 2 | 71.04 ± 1.36* |
| | 3 | 71.11 ± 0.87* |
| | 4 | 69.75 ± 0.98* |
| | 5 | 68.01 ± 1.02* |
| | 6 | 65.68 ± 1.46* |
| | 7 | 58.18 ± 0.94* |
| | 8 | 54.12 ± 1.51* |
| | 9 | 54.05 ± 1.18* |

TABLE 9-continued

| Effects of three-component drug group and seven-component drug group on expression of Foxp3 in spleen regulatory T cells of rats stimulated by LPS (x ± s, n = 6, unit: %) | | |
|---|---|---|
| Group | | 72 h |
| Seven-component drug group | 1 | 66.07 ± 0.78* |
| | 2 | 66.38 ± 1.34* |
| | 3 | 65.91 ± 1.58* |
| | 4 | 64.70 ± 1.40* |
| | 5 | 65.09 ± 1.47* |
| | 6 | 64.19 ± 2.04* |
| | 7 | 64.59 ± 1.15* |
| | 8 | 63.81 ± 1.48* |
| | 9 | 65.39 ± 1.48* |
| | 10 | 59.85 ± 1.61* |
| | 11 | 59.38 ± 1.81* |
| | 12 | 56.11 ± 1.62* |
| | 13 | 55.36 ± 2.59* |
| | 14 | 55.01 ± 2.11* |
| | 15 | 53.32 ± 2.16* |
| | 16 | 53.65 ± 1.23* |
| | 17 | 53.03 ± 0.88* |
| | 18 | 53.57 ± 1.02* |

Note:
*indicated $P < 0.05$ when compared with the model group.

EXAMPLE 8

Evaluation of the effects of three-component drug and seven-component drug on the expression of IL-6 in CLP-induced sepsis rats

TABLE 10

| Orthogonal experimental grouping of three-component drug groups | | | |
|---|---|---|---|
| Group | HSYA | Paeoniflorin | Albiflorin |
| 1 | Low | Low | Low |
| 2 | Low | Moderate | High |
| 3 | Low | High | Moderate |
| 4 | Moderate | Low | High |
| 5 | Moderate | Moderate | Moderate |
| 6 | Moderate | High | Low |
| 7 | High | Low | Moderate |
| 8 | High | Moderate | Low |
| 9 | High | High | High |

In Table 10, the three concentrations of HSYA were low (0.9 μM), moderate (9 μM), and high (90 μM). The three concentrations of paeoniflorin were low (0.9 μM), moderate (9 μM), and high (90 μM). The three concentrations of albiflorin were low (0.09 μM), moderate (0.9 μM), and high (9 μM). The three concentrations of oxypaeoniflorin were low (0.09 μM), moderate (0.9 μM), and high (9 μM. The three concentrations of senkyunolide I were low (0.09 μM), moderate (0.9 μM), and high (9 μM). The three concentrations of SAAS were low (0.09 μM), moderate (0.9 μM), and high (9 μM). The three concentrations of ferulic acid were low (0.009 μM), moderate (0.09 μM), and high (0.9 μM).

TABLE 11

| Orthogonal experimental grouping of seven-component drug groups | | | | | | | |
|---|---|---|---|---|---|---|---|
| Group | HSYA | Paeoniflorin | Albiflorin | Oxypaeoniflorin | Senkyunolide I | SAAS | Ferulic acid |
| 1 | Low | Low | Low | Low | Low | Low | Low |
| 2 | Low | Moderate | Moderate | Moderate | Moderate | Moderate | Moderate |
| 3 | Low | High | High | High | High | High | High |
| 4 | Moderate | Low | Low | Moderate | Moderate | High | High |
| 5 | Moderate | Moderate | Moderate | High | High | Low | Low |
| 6 | Moderate | High | High | Low | Low | Moderate | Moderate |
| 7 | High | Low | Moderate | Low | High | Moderate | High |
| 8 | High | Moderate | High | Moderate | Low | High | Low |
| 9 | High | High | Low | High | Moderate | Low | Moderate |
| 10 | Low | Low | High | High | Moderate | Moderate | Low |
| 11 | Low | Moderate | Low | Low | High | High | Moderate |
| 12 | Low | High | Moderate | Moderate | Low | Low | High |
| 13 | Moderate | Low | Moderate | High | Low | High | Moderate |
| 14 | Moderate | Moderate | High | Low | Moderate | Low | High |
| 15 | Moderate | High | Low | Moderate | High | Moderate | Low |
| 16 | High | Low | High | Moderate | High | Low | Moderate |
| 17 | High | Moderate | Low | High | Low | Moderate | High |
| 18 | High | High | Moderate | Low | Moderate | High | Low |

1. Experimental Materials

Clean-grade male SD rats (180 g to 220 g) were adaptively fed for 1 week. HSYA, paeoniflorin, albiflorin, oxypaeoniflorin, senkyunolide I, SAAS, ferulic acid, and IL-6 ELISA kit were used.

2. Experimental Methods 2.1 Grouping and Intervention 290 rats were randomly divided into 29 groups including a control group, a model group, and a drug treatment group, with 10 rats in each group. The drug treatment group was subjected to an orthogonal experiment, and a grouping method of the orthogonal experiment is shown in Table 10 and Table 11.

The solution preparation method and experimental injection volume were as follows: each rat was calculated as 200 g, and the experimental injection volume was 1.0 mL/time/rat. According to the corresponding concentration of each group in Table 10, the appropriate weight of HSYA, paeoniflorin, and albiflorin were weighed with a precision balance (1/10000 g), combined into different volumetric flasks according to the combinations of different concentrations, and then dissolved in appropriate amount of normal saline (0.9% sodium chloride aqueous solution), respectively, to obtain 9 groups of three-component drugs with corresponding concentrations. According to the corresponding concentration of each group in Table 11, the appropriate weight of HSYA, paeoniflorin, albiflorin, oxypaeoniflorin, senkyunolide I, SAAS, and ferulic acid were weighed with a precision balance (1/10000 g), combined into different volumetric flasks according to the combinations of different concentrations, and then dissolved in appropriate amount of normal saline (0.9% sodium chloride aqueous solution), respectively, to obtain 18 groups of seven-component drugs with corresponding concentrations. Rats were fasted for 12 h before the experiment, weighed and divided into groups according to the random number table method. In the control group, the skin was sutured after the cecum was exposed by laparotomy, and 10 mL of normal saline was injected subcutaneously for resuscitation. After cecal ligation and puncture (CLP) was conducted in the model group and the drug treatment group, 10 mL of normal saline was subcutaneously injected for resuscitation. CLP modeling included: a mixture prepared with ketamine injection+Sumianxin II injection at a volume ratio of 2:1 was injected intramuscularly to anesthetize the rats, and the animal model of sepsis was prepared by the CLP. The junction of the cecum and ileum was ligated, and a 18-gauge needle was used to penetrate the cecum twice to form an intestinal fistula, and two drainage strips (0.5 cm×2.0 cm) were left in place to prevent the needle holes from healing, and then the skin was sutured layer by layer. After the operation, the rats were immediately subcutaneously injected with 10 mL of normal saline for resuscitation. After the CLP operation of the rats, the drug treatment group was injected with the above-mentioned different medicinal solutions through the tail vein at 2 h, 12 h, 24 h, 36 h, 48 h, and 60 h after the operation; the model group and the control group were injected with normal saline through the tail vein at the corresponding time. The experiment was repeated up to n=10.

2.2 Blood Collection and Testing

At 8 h, 24 h, and 48 h after CLP, the animals in each group were anesthetized, and 3 mL of aseptic blood was collected from the abdominal aorta, and plasma IL-6 content was detected by ELISA.

3. Experimental Results

The experimental results (Table 12) showed that the plasma of the control group contained a small amount of IL-6; in the early stage after CLP operation, the IL-6 content in the model group increased significantly, and the IL-6 level further increased at 8 h, and gradually decreased at 24 h; 48 hours after operation, IL-6 level in the model group was still higher than that in the control group, and the differences were statistically significant ($p<0.05$). However, the plasma levels of IL-6 in the treatment group at 8 h, 24 h, and 48 h after operation were significantly lower than those in the model group ($p<0.05$), and were close to the level in the control group.

The above findings indicated that compared with the model group, the three-component drug and the seven-component drug in each dosage group could significantly reduce the expression of IL-6 in CLP sepsis rats. This suggested that the drug had a significant inhibitory effect on the early inflammatory response of the sepsis rat model. The converted approximate adult human dosages were: three-component drug group (HSYA 6 mg to 600 mg, paeoniflorin 6 mg to 600 mg, and albiflorin 0.6 mg to 60 mg); seven-component drug group (HSYA 6 mg to 600 mg, paeoniflorin 6 mg to 600 mg, albiflorin 0.6 mg to 60 mg, oxypaeoniflorin 0.6 mg to 60 mg, senkyunolide I 0.6 mg to 60 mg, SAAS 0.6 mg to 60 mg, and ferulic acid 0.06 mg to 6 mg). According to the "*Pharmacological Experimental Methodology*" edited by Shuyun Xu, it was calculated according to the body surface area conversion method between humans and animals, human dosage=rat dosage/0.018 (based on adult body weight of 70 kg and rat body weight of 0.2 kg).

TABLE 12

Effects of three-component drug group and seven-component drug group on IL-6 expression in CLP-induced sepsis rats ($\bar{x} \pm s$, n = 10, unit: pg/mL)

| Group | | 8 h | 24 h | 48 h |
|---|---|---|---|---|
| Control group | | 109.79 ± 2.86* | 111.94 ± 2.43* | 110.03 ± 3.60* |
| Model group | | 250.47 ± 3.29 | 280.14 ± 3.14 | 259.82 ± 4.43 |
| Three-component drug group | 1 | 209.59 ± 2.79* | 249.47 ± 3.86* | 240.08 ± 4.30* |
| | 2 | 190.26 ± 3.10* | 219.20 ± 6.25* | 210.30 ± 5.26* |
| | 3 | 189.72 ± 3.68* | 219.46 ± 3.54* | 208.07 ± 3.64* |
| | 4 | 189.21 ± 3.58* | 219.71 ± 5.37* | 208.92 ± 2.92* |
| | 5 | 191.20 ± 2.69* | 217.18 ± 3.17* | 208.42 ± 3.48* |
| | 6 | 190.41 ± 2.98* | 221.06 ± 4.74* | 209.19 ± 4.43* |
| | 7 | 189.59 ± 2.53* | 219.43 ± 5.39* | 209.03 ± 3.83* |
| | 8 | 191.50 ± 2.99* | 219.95 ± 4.74* | 206.77 ± 3.55* |
| | 9 | 167.96 ± 4.10* | 189.36 ± 3.73* | 178.38 ± 4.07* |
| Seven-component drug group | 1 | 211.54 ± 3.65* | 218.80 ± 4.59* | 210.28 ± 2.46* |
| | 2 | 181.26 ± 4.32* | 199.51 ± 4.46* | 179.59 ± 3.57* |
| | 3 | 183.41 ± 4.64* | 202.33 ± 4.22* | 180.13 ± 3.92* |
| | 4 | 180.63 ± 4.31* | 202.29 ± 3.86* | 180.19 ± 4.85* |
| | 5 | 181.95 ± 5.15* | 199.63 ± 3.86* | 181.41 ± 3.26* |
| | 6 | 182.43 ± 4.01* | 198.05 ± 1.94* | 179.47 ± 4.53* |
| | 7 | 183.23 ± 4.89* | 202.77 ± 5.34* | 179.78 ± 2.87* |
| | 8 | 182.77 ± 4.90* | 200.05 ± 4.43* | 180.79 ± 4.30* |
| | 9 | 182.51 ± 3.26* | 201.26 ± 4.09* | 177.18 ± 2.49* |
| | 10 | 181.53 ± 4.28* | 201.99 ± 4.94* | 178.23 ± 3.64* |
| | 11 | 181.21 ± 4.84* | 203.40 ± 4.99* | 178.79 ± 4.13* |
| | 12 | 182.73 ± 5.35* | 199.75 ± 4.00* | 175.95 ± 2.55* |
| | 13 | 181.65 ± 3.95* | 201.98 ± 4.31* | 180.27 ± 4.05* |
| | 14 | 182.45 ± 3.66* | 199.05 ± 3.98* | 179.97 ± 4.72* |
| | 15 | 182.83 ± 3.70* | 200.65 ± 4.84* | 179.48 ± 3.93* |
| | 16 | 180.24 ± 3.66* | 203.07 ± 2.61* | 179.77 ± 4.25* |
| | 17 | 181.92 ± 5.11* | 202.58 ± 5.00* | 178.36 ± 3.06* |
| | 18 | 149.16 ± 3.47* | 170.53 ± 3.20* | 158.49 ± 4.17* |

Note:
*indicated $P < 0.05$ when compared with the model group.

EXAMPLE 9

Evaluation of the effects of three-component drug and seven-component drug on the expression of HMGB1 in CLP-induced sepsis rats

1. Experimental Materials

Clean-grade male SD rats (180 g to 220 g) were adaptively fed for 1 week. HSYA, paeoniflorin, albiflorin, oxypaeoniflorin, senkyunolide I, SAAS, ferulic acid, and HMGB1 ELISA kit were used.

2. Experimental Methods 2.1 Grouping and Intervention

The method was the same as that in Example 8.

2.2 Blood Collection and Testing

At 48 h and 72 h after CLP, the animals in each group were anesthetized, and 3 mL of aseptic blood was collected from the abdominal aorta, and the plasma HMGB1 content was detected by ELISA.

3. Experimental Results

The experimental results (Table 13) showed that the plasma of the control group contained a small amount of HMGB1; in the late stage after CLP, the HMGB1 content of the model group increased significantly, and gradually increased after 48 h; at 72 h after operation, the model group was still higher than the control group, and the differences were statistically significant (p<0.05). However, the plasma levels of HMGB1 in the drug treatment group at 48 h and 72 h after operation were significantly lower than those in the model group (p<0.05), and were close to the level of the control group. The above findings indicated that the three-component drug and seven-component drug in each dosage group could significantly reduce the expression of HMGB1 in CLP sepsis rats compared with the model group. This suggested that the three-component drug and the seven-component drug had inhibitory effects on advanced stage inflammatory factors in the sepsis rat model. The converted approximate adult human dosages were: three-component drug group (HSYA 6 mg to 600 mg, paeoniflorin 6 mg to 600 mg, and albiflorin 0.6 mg to 60 mg); seven-component drug group (HSYA 6 mg to 600 mg, paeoniflorin 6 mg to 600 mg, albiflorin 0.6 mg to 60 mg, oxypaeoniflorin 0.6 mg to 60 mg, senkyunolide I 0.6 mg to 60 mg, SAAS 0.6 mg to 60 mg, and ferulic acid 0.06 mg to 6 mg). According to the "*Pharmacological Experimental Methodology*" edited by Shuyun Xu, it was calculated according to the body surface area conversion method between humans and animals, human dosage=rat dosage/0.018 (based on adult body weight of 70 kg and rat body weight of 0.2 kg).

TABLE 13

Effects of three-component drug group and seven-component drug group on HMGB1 expression in CLP-induced sepsis rats (x ± s, n = 10, unit: pg/mL)

| Group | | 72 h |
|---|---|---|
| Control group | | 8.77 ± 1.38* |
| Model group | | 46.04 ± 2.17 |
| Three-component drug group | 1 | 35.81 ± 2.15* |
| | 2 | 30.49 ± 2.10* |
| | 3 | 29.96 ± 2.06* |
| | 4 | 30.11 ± 2.39* |
| | 5 | 29.54 ± 2.09* |
| | 6 | 31.04 ± 2.27* |
| | 7 | 30.00 ± 1.93* |
| | 8 | 29.74 ± 2.53* |
| | 9 | 25.53 ± 1.64* |
| Seven-component drug group | 1 | 30.81 ± 2.39* |
| | 2 | 24.33 ± 2.02* |
| | 3 | 26.01 ± 1.95* |
| | 4 | 25.92 ± 1.82* |
| | 5 | 26.09 ± 1.48* |
| | 6 | 24.93 ± 1.93* |
| | 7 | 24.72 ± 2.53* |
| | 8 | 24.72 ± 2.33* |
| | 9 | 25.17 ± 2.60* |
| | 10 | 24.76 ± 1.97* |
| | 11 | 24.95 ± 1.85* |
| | 12 | 25.70 ± 1.50* |
| | 13 | 25.57 ± 2.39* |
| | 14 | 25.65 ± 1.98* |
| | 15 | 25.79 ± 2.06* |
| | 16 | 25.44 ± 2.32* |

TABLE 13-continued

Effects of three-component drug group and seven-component drug group on HMGB1 expression in CLP-induced sepsis rats (x ± s, n = 10, unit: pg/mL)

| Group | | 72 h |
|---|---|---|
| | 17 | 25.50 ± 1.97* |
| | 18 | 21.24 ± 1.98* |

Note:
*indicated P < 0.05 when compared with the model group.

EXAMPLE 10

Evaluation of the effects of three-component drug and seven-component drug on the release of TF in CLP-induced sepsis rats

1. Experimental Materials

Clean-grade male SD rats (180 g to 220 g) were adaptively fed for 1 week. HSYA, paeoniflorin, albiflorin, oxypaeoniflorin, senkyunolide I, SAAS, ferulic acid, and TF ELISA kit were used.

2. Experimental Methods 2.1 Grouping and Intervention

The method was the same as that in Example 8.

2.2 Blood Collection and Testing

At 12 h, 24 h, 48 h, and 72 h after CLP, the animals in each group were anesthetized, and 5 mL of aseptic blood was collected from the abdominal aorta. The TF content was detected by ELISA.

3. Experimental Results

The experimental results (Table 14) showed that there was certain expression of TF in monocytes in the control group; the expression of TF in the model group (12 h, 24 h, 48 h, and 72 h after operation) was significantly higher than that in the control group (p<0.05), and gradually increased with the prolongation of postoperative time. The expression of TF in the drug treatment group (12 h, 24 h, 48 h, and 72 h after operation) was significantly lower than that in the model group (p<0.05). The above findings suggested that compared with the model group, the three-component drug and the seven-component drug in each dosage group could significantly reduce the release of TF in CLP sepsis rats. This showed that the three-component drug and the seven-component drug could significantly inhibit the release of coagulation factors and improve the hypercoagulable state in the rat model of sepsis. The converted approximate adult human dosages were: three-component drug group (HSYA 6 mg to 600 mg, paeoniflorin 6 mg to 600 mg, and albiflorin 0.6 mg to 60 mg); seven-component drug group (HSYA 6 mg to 600 mg, paeoniflorin 6 mg to 600 mg, albiflorin 0.6 mg to 60 mg, oxypaeoniflorin 0.6 mg to 60) mg, senkyunolide I 0.6 mg to 60 mg, SAAS 0.6 mg to 60 mg, and ferulic acid 0.06 mg to 6 mg).

TABLE 14

Effects of three-component drug group and seven-component drug group on TF release in CLP-induced sepsis rats (x ± s, n = 10, unit: pg/mL)

| Group | | 12 h after operation | 24 h after operation | 48 h after operation | 72 h after operation |
|---|---|---|---|---|---|
| Control group | | 200.75 ± 5.25* | 212.44 ± 10.69* | 210.69 ± 12.28* | 219.73 ± 9.70* |
| Model group | | 218.03 ± 15.82 | 248.17 ± 19.99 | 340.61 ± 15.30 | 316.46 ± 21.51 |
| Three-component drug group | 1 | 205.77 ± 9.10* | 231.71 ± 14.30* | 268.90 ± 17.49* | 262.32 ± 20.41* |
| | 2 | 203.76 ± 8.69* | 232.83 ± 11.23* | 267.09 ± 13.37* | 263.85 ± 16.67* |
| | 3 | 204.31 ± 6.98* | 233.45 ± 18.23* | 264.59 ± 20.43* | 276.09 ± 19.99* |
| | 4 | 206.81 ± 10.71* | 235.63 ± 18.22* | 259.25 ± 8.58* | 263.15 ± 11.46* |
| | 5 | 204.32 ± 10.04* | 232.91 ± 13.82* | 265.95 ± 8.80* | 261.04 ± 14.77* |
| | 6 | 205.63 ± 6.77* | 230.61 ± 15.58* | 264.36 ± 9.16* | 264.31 ± 12.44* |
| | 7 | 201.27 ± 4.57* | 225.45 ± 12.25* | 230.83 ± 11.36* | 264.82 ± 16.54* |
| | 8 | 201.57 ± 6.21* | 218.20 ± 13.81* | 235.01 ± 13.13* | 261.47 ± 17.11* |
| | 9 | 201.47 ± 6.93* | 225.46 ± 11.29* | 231.37 ± 12.11* | 263.92 ± 20.06* |
| Seven-component drug group | 1 | 206.56 ± 11.18* | 226.84 ± 13.57* | 269.10 ± 16.73* | 272.74 ± 13.20* |
| | 2 | 203.78 ± 5.80* | 223.12 ± 13.85* | 258.85 ± 19.10* | 258.03 ± 11.09* |
| | 3 | 203.92 ± 5.83* | 221.37 ± 12.48* | 258.73 ± 18.88* | 262.93 ± 15.10* |
| | 4 | 203.57 ± 6.70* | 221.20 ± 15.64* | 260.95 ± 18.60* | 270.28 ± 14.60* |
| | 5 | 203.83 ± 6.90* | 224.84 ± 13.90* | 249.47 ± 17.09* | 271.82 ± 16.01* |
| | 6 | 202.52 ± 4.65* | 220.76 ± 10.51* | 262.17 ± 13.96* | 261.06 ± 14.13* |
| | 7 | 203.53 ± 4.72* | 224.39 ± 11.96* | 262.49 ± 21.74* | 266.46 ± 16.34* |
| | 8 | 203.68 ± 7.39* | 219.36 ± 12.50* | 251.98 ± 19.13* | 254.96 ± 10.23* |
| | 9 | 204.94 ± 4.62* | 220.57 ± 11.97* | 257.70 ± 15.48* | 262.85 ± 11.16* |
| | 10 | 204.34 ± 6.70* | 223.27 ± 15.18* | 265.45 ± 22.88* | 268.18 ± 15.57* |
| | 11 | 202.09 ± 4.53* | 223.56 ± 14.86* | 260.44 ± 21.96* | 270.95 ± 15.40* |
| | 12 | 203.32 ± 4.85* | 217.28 ± 14.66* | 263.44 ± 21.70* | 262.15 ± 19.84* |
| | 13 | 203.28 ± 4.97* | 217.47 ± 14.28* | 259.01 ± 20.01* | 263.37 ± 14.00* |
| | 14 | 203.00 ± 6.59* | 224.99 ± 12.91* | 260.50 ± 19.32* | 266.70 ± 12.30* |
| | 15 | 202.62 ± 6.71* | 222.32 ± 13.94* | 265.86 ± 21.31* | 273.18 ± 12.49* |
| | 16 | 204.57 ± 5.18* | 221.68 ± 13.03* | 263.94 ± 19.09* | 273.34 ± 15.98* |
| | 17 | 204.36 ± 6.50* | 217.14 ± 11.68* | 265.88 ± 18.00* | 265.85 ± 12.98* |
| | 18 | 202.06 ± 7.19* | 219.87 ± 15.54* | 250.36 ± 20.40* | 256.04 ± 10.03* |

Note:
*indicated P < 0.05 when compared with the model group.

EXAMPLE 11

Evaluation of the effects of three-component drug and seven-component drug on the release of TM in CLP-induced sepsis rats

1. Experimental Materials

Clean-grade male SD rats (180 g to 220 g) were adaptively fed for 1 week. HSYA, paeoniflorin, albiflorin, oxypaeoniflorin, senkyunolide I, SAAS, ferulic acid, and TM ELISA kit were used.

2. Experimental Methods 2.1 Grouping and Intervention

The method was the same as that in Example 8.

2.2 Blood Collection and Testing

At 12 h, 24 h, 48 h, and 72 h after CLP, the animals in each group were anesthetized, and 5 mL of aseptic blood was collected from the abdominal aorta. The TM content was detected by ELISA.

3. Experimental Results

The experimental results (Table 15) showed that there was certain expression of TM in monocytes in the control group; the expression of TM in the model group (12 h, 24 h, 48 h, and 72 h after operation) was significantly higher than that in the control group ($p<0.05$), and gradually increased with the prolongation of postoperative time. The expression of TM in the drug treatment group (12 h, 24 h, 48 h, and 72 h after operation) was significantly lower than that in the model group ($p<0.05$). The above findings suggested that, compared with the model group, the three-component drug and the seven-component drug in each dosage group could significantly reduce the release of TM in CLP sepsis rats. This showed that the three-component drug and the seven-component drug could significantly inhibit the release of coagulation factors and improve the hypercoagulable state in the rat model of sepsis. The converted approximate adult human dosages were: three-component drug group (HSYA 6 mg to 600 mg, paeoniflorin 6 mg to 600 mg, and albiflorin 0.6 mg to 60 mg); seven-component drug group (HSYA 6 mg to 600 mg, paeoniflorin 6 mg to 600 mg, albiflorin 0.6 mg to 60 mg, oxypaeoniflorin 0.6 mg to 60 mg, senkyunolide I 0.6 mg to 60 mg, SAAS 0.6 mg to 60 mg, and ferulic acid 0.06 mg to 6 mg). According to the "*Pharmacological Experimental Methodology*" edited by Shuyun Xu, it was calculated according to the body surface area conversion method between humans and animals, human dosage=rat dosage/0.018 (based on adult body weight of 70 kg and rat body weight of 0.2 kg).

TABLE 15

Effects of three-component drug group and seven-component drug group on TM release in CLP-induced sepsis rats ($\bar{x} \pm s$, n = 10, unit: pg/mL)

| Group | | 12 h after operation | 24 h after operation | 48 h after operation | 72 h after operation |
|---|---|---|---|---|---|
| Control group | | 20.96 ± 1.02* | 21.56 ± 1.46* | 23.57 ± 1.56* | 22.54 ± 1.89* |
| Model group | | 25.76 ± 1.39 | 26.59 ± 1.94 | 31.17 ± 2.05 | 30.09 ± 1.89 |
| Three-component drug group | 1 | 23.17 ± 1.69* | 23.32 ± 1.51* | 27.02 ± 1.92* | 24.68 ± 1.34* |
| | 2 | 22.60 ± 1.98* | 23.16 ± 1.56* | 26.26 ± 1.86* | 23.56 ± 0.98* |
| | 3 | 23.25 ± 1.67* | 23.90 ± 1.33* | 26.29 ± 1.91* | 24.51 ± 1.37* |
| | 4 | 21.25 ± 1.36* | 22.85 ± 1.28* | 24.96 ± 1.53* | 24.38 ± 1.46* |
| | 5 | 21.33 ± 1.98* | 22.94 ± 1.72* | 25.95 ± 2.17* | 24.52 ± 1.49* |
| | 6 | 20.64 ± 1.72* | 22.54 ± 1.71* | 24.72 ± 1.22* | 24.39 ± 1.85* |
| | 7 | 20.70 ± 1.40* | 22.22 ± 1.42* | 25.63 ± 1.71* | 24.85 ± 1.34* |
| | 8 | 21.23 ± 1.98* | 22.70 ± 1.66* | 25.78 ± 1.81* | 23.97 ± 1.22* |
| | 9 | 21.40 ± 1.72* | 22.63 ± 1.50* | 25.56 ± 2.18* | 24.21 ± 1.70* |
| Seven-component drug group | 1 | 23.55 ± 1.79* | 23.58 ± 1.42* | 27.34 ± 2.67* | 27.77 ± 0.94* |
| | 2 | 22.28 ± 1.17* | 22.47 ± 1.44* | 27.11 ± 2.21* | 26.55 ± 1.76* |
| | 3 | 22.87 ± 1.29* | 22.86 ± 1.82* | 25.75 ± 1.74* | 26.17 ± 1.84* |
| | 4 | 22.52 ± 1.40* | 23.18 ± 1.61* | 26.18 ± 1.61* | 27.16 ± 1.82* |
| | 5 | 22.19 ± 1.57* | 22.80 ± 1.14* | 26.38 ± 2.09* | 26.78 ± 1.23* |
| | 6 | 22.02 ± 1.70* | 22.32 ± 1.54* | 27.26 ± 1.88* | 26.27 ± 1.65* |
| | 7 | 22.35 ± 1.46* | 23.26 ± 1.42* | 26.52 ± 1.89* | 26.71 ± 1.60* |
| | 8 | 22.08 ± 1.52* | 23.01 ± 1.75* | 26.10 ± 2.19* | 26.25 ± 1.94* |
| | 9 | 22.23 ± 1.44* | 22.91 ± 1.76* | 26.42 ± 1.95* | 26.60 ± 1.45* |
| | 10 | 22.55 ± 1.73* | 22.71 ± 1.26* | 26.66 ± 2.44* | 27.12 ± 0.86* |
| | 11 | 22.49 ± 0.86* | 22.28 ± 1.29* | 26.84 ± 2.39* | 26.50 ± 1.46* |
| | 12 | 21.93 ± 1.31* | 22.74 ± 1.37* | 27.24 ± 2.40* | 26.56 ± 1.48* |
| | 13 | 21.35 ± 1.28* | 22.53 ± 1.25* | 25.99 ± 1.81* | 27.03 ± 1.63* |
| | 14 | 22.49 ± 1.70* | 22.29 ± 1.42* | 25.83 ± 1.67* | 26.31 ± 1.39* |
| | 15 | 22.10 ± 1.74* | 22.82 ± 1.19* | 26.08 ± 1.98* | 26.95 ± 1.41* |
| | 16 | 22.74 ± 1.47* | 21.89 ± 1.44* | 26.26 ± 2.00* | 26.18 ± 1.47* |
| | 17 | 21.57 ± 1.11* | 22.60 ± 1.33* | 26.76 ± 2.15* | 26.66 ± 1.43* |
| | 18 | 21.76 ± 1.34* | 21.94 ± 1.24* | 25.64 ± 1.89* | 26.28 ± 1.13*o |

Note:
*indicated P < 0.05 when compared with the model group.

EXAMPLE 12

Evaluation of the effects of three-component drug and seven-component drug on the function of regulatory T cells in CLP-induced sepsis rats

1. Experimental Materials

Clean-grade male SD rats (180 g to 220 g), LPS, HSYA, paeoniflorin, albiflorin, oxypaeoniflorin, senkyunolide I, SAAS, ferulic acid, 1640 medium, 24-well plate, phycoerythrin (PE)-anti-rat CD25, fluorescein isothiocyanate (FITC)-labeled anti-rat CD4, and fluorescein isothiocyanate (FITC)-labeled annexin V apoptosis kit; rat anti-PE kit, CD4 magnetic beads, MiniMACS magnetic separation instrument, and separation column; PE-labeled Foxp3 kit, PE-labeled CTLA-4 kit, anti-rat CD3 monoclonal antibody, and anti-rat CD28 monoclonal antibody.

2. Experimental Methods 2.1 Grouping and Intervention

The method was the same as that in Example 8.

2.2 Cell Isolation and Culture 72 h after CLP, the rats were sacrificed by neck dislocation, the chest and abdomen were disinfected three times with alcohol cotton balls, and the abdomen was opened to preserve a complete peritoneum. The peritoneum was disinfected again with alcohol cotton balls, and opened with another pair of tweezers, and the spleen was removed and placed in 15 ml of PBS at 4° C. The capsule of the spleen was torn off with tweezers, put into a strainer, moistened with PBS, and the spleen was torn up, and the fascia was removed. The spleen was ground with a plunger of a sterile syringe, a resulting suspension was pipetted into a centrifuge tube, centrifuged at 1,200 rpm for 7 min, and a supernatant was discarded. An appropriate amount of the MACS Buffer (10 mL/spleen) was added to resuspend. A resuspended product was added to an upper layer of a lymphocyte separation medium (1:1) along the tube wall, and centrifuged at 3,000 rpm for 15 min. An obtained middle-layer liquid was aspirated with a straw, put into another centrifuge tube, a cleaning solution was added, centrifugation was conducted at 1,200 rpm for 7 min, and a supernatant was discarded. The MACS Buffer was added to resuspend for later use.

1 μL of the anti-CD25-APC antibody was added into per $1\times10^7$ monocytes, incubated at 4° C. for 15 min, and washed with the MACS Buffer. 20 μL of the anti-APC magnetic beads and 80 μL of the MACS Buffer were added into per $1\times10^7$ cells, incubated at 4° C. for 15 min, washed with the MACS Buffer, and resuspended with an appropriate amount of the MACS Buffer, and CD25+ cells were obtained by magnetic separation on the LS column.

After the CD25+ cells were counted, 20 μL of a dissociation agent was added to per $1\times10^7$ cells, incubated at 4° C. for 10 min, and washed with MACS Buffer. 20 μL of the anti-CD4 magnetic beads and 30 μL of a terminator were added per $1\times10^7$ cells, incubated at 4° C. for 15 min, and washed with the MACS Buffer. An appropriate amount of the MACS Buffer was added to resuspend, and magnetic separation was conducted on an LS column to obtain CD4+ CD25+ cells.

2.3 Detection and Analysis

Detection of Treg apoptosis rate: the cells were collected, washed with pre-cooled PBS, and washed with 1 ml of a 1×Binding Buffer, centrifuged, and a supernatant was removed. 5 μL of the FITC Annexin V and 5 μL of PI were added to the remaining 100 μL of cells, and incubated at room temperature (25° C.) in the dark for 15 min. 200 μL of the 1×Binding Buffer was added into the cells, mixed well, and detected by flow cytometer within 1 h.

Detection of Foxp3 and CTLA-4 expression: after the cell supernatant was collected, the cells were washed with PBS, the supernatant was removed, a CTLA-4-PE fluorescent antibody was added, incubated at 4° C. in the dark for 30 min, and a membrane-breaking agent was added overnight. The next day, the cells were washed with a membrane-breaking buffer, and a supernatant was removed. A Foxp3-PE-Cy7 fluorescent antibody was added, incubated at room temperature in the dark for 30 min, washed with the membrane-breaking buffer, and a supernatant was removed. The cells were immobilized with 1% paraformaldehyde and detected by flow cytometry.

3. Experimental Results

3.1 Effects of Three-Component Drug and Seven-Component Drug on the Function of Regulatory T Cells in CLP-Induced Sepsis Rats The experimental results (Table 16) showed that an apoptosis rate of Tregs in the model group was significantly lower than that in the control group ($p<0.05$), and an apoptosis rate of Tregs in the drug treatment group was significantly higher than that in the model group ($p<0.05$). The expressions of Foxp3 and CTLA-4 in the model group were significantly higher than those in the control group ($p<0.05$), and those in the drug treatment group were significantly lower than those in the model group ($p<0.05$). The above findings suggested that compared with the model group, the three-component drug and the seven-component drug of each dosage group could promote the apoptosis of Tregs in sepsis, and had an inhibitory effect of down-regulating the proliferation and secretion function of T lymphocytes. This showed that the three-component drug and the seven-component drug in each dosage group had an obvious effect on correcting the immune suppression state of the body's cells in the rat model of sepsis. The converted approximate adult human dosages were: three-component drug group (HSYA 6 mg to 600 mg, paeoniflorin 6 mg to 600 mg, and albiflorin 0.6 mg to 60 mg); seven-component drug group (HSYA 6 mg to 600 mg, paeoniflorin 6 mg to 600 mg, albiflorin 0.6 mg to 60 mg, oxypaeoniflorin 0.6 mg to 60 mg, senkyunolide I 0.6 mg to 60 mg, SAAS 0.6 mg to 60 mg, and ferulic acid 0.06 mg to 6 mg). According to the "*Pharmacological Experimental Methodology*" edited by Shuyun Xu, it was calculated according to the body surface area conversion method between humans and animals, human dosage=rat dosage/0.018 (based on adult body weight of 70 kg and rat body weight of 0.2 kg).

TABLE 16

Effects of three-component drug and seven-component drug on apoptosis rate of regulatory T cells and expressions of Foxp3 and CTLA-4 in sepsis rats (x ± s, n = 10, unit: %)

| Group | | T cell apoptosis rate | Ctla-4 | Foxp3 |
|---|---|---|---|---|
| Control group | | 40.01 ± 3.79* | 11.19 ± 1.58* | 38.11 ± 3.80* |
| Model group | | 10.15 ± 2.63 | 48.31 ± 4.06 | 89.46 ± 3.61 |
| Three- | 1 | 16.21 ± 1.75* | 34.48 ± 3.01* | 82.10 ± 2.54* |
| component | 2 | 21.98 ± 3.50* | 29.68 ± 3.63* | 69.39 ± 3.32* |
| drug | 3 | 21.11 ± 3.47* | 31.03 ± 2.60* | 71.08 ± 4.22* |
| group | 4 | 20.68 ± 3.76* | 29.18 ± 2.68* | 68.49 ± 3.15* |
| | 5 | 20.40 ± 3.67* | 26.93 ± 1.65* | 71.04 ± 2.99* |
| | 6 | 21.87 ± 2.26* | 32.90 ± 2.54* | 70.48 ± 3.71* |
| | 7 | 22.65 ± 3.01* | 31.30 ± 3.56* | 68.14 ± 3.53* |
| | 8 | 22.08 ± 3.06* | 30.24 ± 3.77* | 69.83 ± 3.08* |
| | 9 | 25.44 ± 3.13* | 25.86 ± 3.11* | 60.41 ± 3.22* |
| Seven- | 1 | 20.97 ± 2.84* | 32.37 ± 2.38* | 70.11 ± 2.87* |
| component | 2 | 24.84 ± 3.55* | 25.56 ± 3.74* | 59.90 ± 3.11* |
| drug | 3 | 25.14 ± 4.21* | 28.39 ± 1.89* | 61.68 ± 3.80* |
| group | 4 | 25.15 ± 2.92* | 24.15 ± 3.64* | 59.40 ± 3.58* |
| | 5 | 25.51 ± 3.17* | 24.61 ± 3.21* | 58.85 ± 4.04* |
| | 6 | 25.42 ± 3.31* | 25.24 ± 3.91* | 59.55 ± 3.28* |
| | 7 | 26.28 ± 2.53* | 25.43 ± 3.20* | 59.96 ± 2.69* |
| | 8 | 26.60 ± 3.58* | 25.38 ± 3.34* | 60.12 ± 3.02* |
| | 9 | 25.49 ± 3.64* | 25.01 ± 3.37* | 57.13 ± 2.80* |
| | 10 | 26.72 ± 2.93* | 27.61 ± 2.97* | 59.57 ± 3.73* |
| | 11 | 26.16 ± 2.92* | 23.97 ± 3.33* | 59.83 ± 3.78* |
| | 12 | 26.41 ± 3.14* | 25.71 ± 3.01* | 58.19 ± 2.67* |
| | 13 | 26.47 ± 3.35* | 26.78 ± 2.59* | 59.27 ± 3.37* |
| | 14 | 25.40 ± 3.23* | 26.19 ± 3.81* | 56.96 ± 2.70* |
| | 15 | 25.71 ± 3.11* | 26.55 ± 3.28* | 58.29 ± 4.39* |
| | 16 | 25.52 ± 3.87* | 26.65 ± 3.57* | 61.26 ± 3.11* |
| | 17 | 25.93 ± 3.41* | 25.69 ± 3.07* | 58.53 ± 3.43* |
| | 18 | 29.09 ± 3.17* | 19.96 ± 3.44* | 48.11 ± 3.52* |

Note:
*indicated P < 0.05 when compared with the model group.

The above description of examples is merely provided to help understand the method of the present disclosure and the core idea thereof. It should be noted that, several improvements and modifications may be made by a person of ordinary skill in the art without departing from the principle of the present disclosure, and these improvements and modifications should also fall within the protection scope of the present disclosure. Various amendments to these embodiments are apparent to those of professional skill in the art, and the general principles defined herein may be implemented in other embodiments without departing from the spirit or scope of the present disclosure. Thus, the present disclosure is not limited to the embodiments shown herein but falls within the widest scope commensurate with the principles and novel features disclosed herein.

What is claimed is:

1. The pharmaceutical composition for treating sepsis consisting of the following seven components as active ingredients: hydroxysafflor yellow A (HSYA) with a structural formula shown in formula I, paeoniflorin with a structural formula shown in formula II, and albiflorin with a structural formula shown in formula III; oxypaeoniflorin with a structural formula shown in formula IV, senkyunolide I with a structural formula shown in formula V, salvianic acid A sodium (SAAS) with a structural formula shown in formula VI, and ferulic acid with a structural formula shown in formula VII; wherein the HSYA, the paeoniflorin, and the albiflorin are present in a mass ratio of (1-100):(1-100):(0.1-10); and the HSYA, the paeoniflorin, the albiflorin, the oxypaeoniflorin, the senkyunolide I, the SAAS, and the ferulic acid are present in a mass ratio of (1-100):(1-100):(1-10):(0.1-10):(0.1-10):(0.1-10):(0.01-1);

formula I

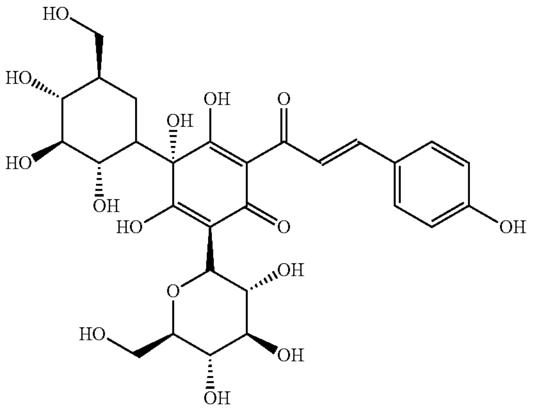

formula II

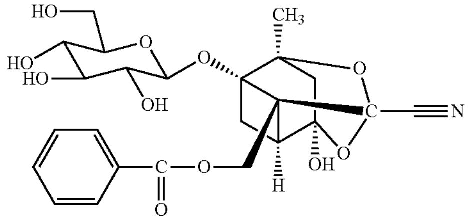

formula III

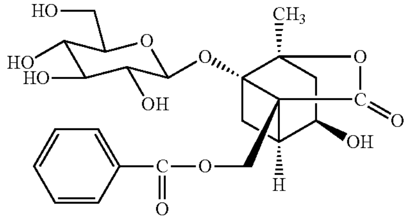

formula IV

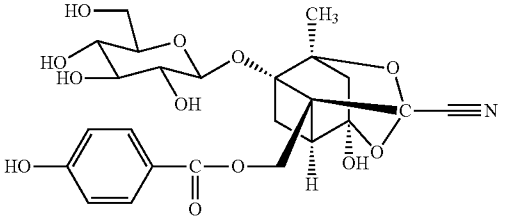

formula V

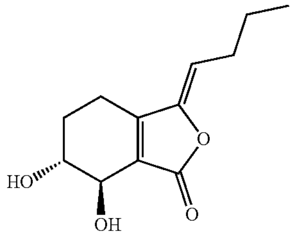

formula VI

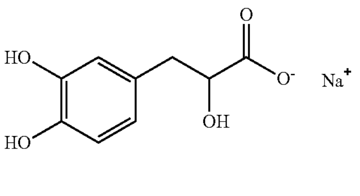

-continued formula VII

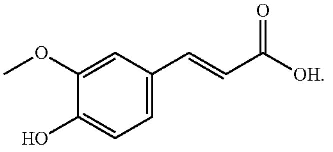

2. The pharmaceutical composition for treating sepsis according to claim 1, wherein the HSYA, the paeoniflorin, the albiflorin, the oxypaeoniflorin, the senkyunolide I, the SAAS, and the ferulic acid are present in a mass ratio of (1-100):(1-100):(1-10):(1-10):(1-10):(1-10):(0.1-1).

3. A pharmaceutical composition for treating sepsis, consisting of the following three components as active ingredients: hydroxysafflor yellow A (HSYA) with a structural formula shown in formula I, paeoniflorin with a structural formula shown in formula II, and albiflorin with a structural formula shown in formula III; wherein the HSYA, the paeoniflorin, and the albiflorin are present in a mass ratio of (1-100):(1-100):(0.1-10);

formula I

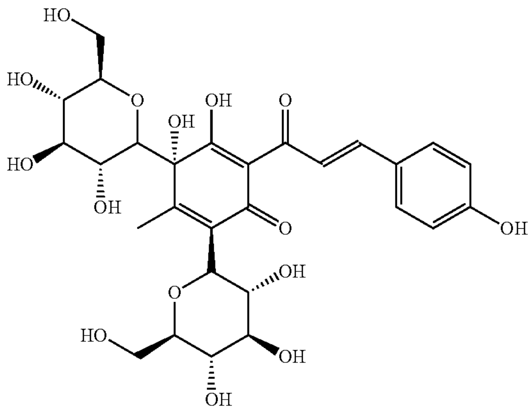

formula II

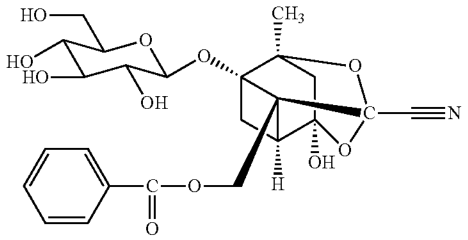

formula III

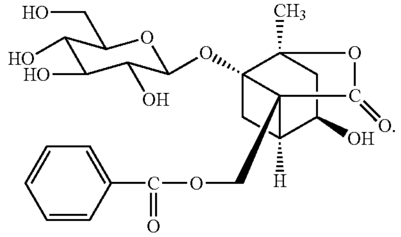

4. The pharmaceutical composition for treating sepsis according to claim 3, wherein the HSYA, the paeoniflorin, and the albiflorin are present in a mass ratio of (1-100):(1-100):(1-10).

5. A method for treating sepsis, comprising: administering a drug prepared from the pharmaceutical composition according to claim 1 to a patient in need.

6. A method for treating sepsis, comprising: administering a drug prepared from the pharmaceutical composition according to claim 1 to a patient in need, wherein the pharmaceutical composition comprises seven active compounds of the HSYA, the paeoniflorin, the albiflorin, the oxypaeoniflorin, the senkyunolide I, the SAAS, and the ferulic acid, 6 mg/kg to 600 mg/kg of the HSYA, 6 mg/kg to 600 mg/kg of the paeoniflorin, 0.6 mg/kg to 60 mg/kg of the albiflorin, 0.6 mg/kg to 60 mg/kg of the oxypaeoniflorin, 0.6 mg/kg to 60 mg/kg of the senkyunolide I, 0.6 mg/kg to 60 mg/kg of the SAAS, and 0.06 mg/kg to 6 mg/kg of the ferulic acid are used.

7. A method for treating sepsis, comprising: administering a drug prepared from the pharmaceutical composition according to claim 2 to a patient in need.

8. A method for treating sepsis, comprising: administering a drug prepared from the pharmaceutical composition according to claim 3 to a patient in need.

9. The method for treating sepsis according to claim 8, wherein the pharmaceutical composition comprises three active compounds of the HSYA, the paeoniflorin, and the albiflorin, 6 mg/kg to 600 mg/kg of the HSYA, 6 mg/kg to 600 mg/kg of the paeoniflorin, and 0.6 mg/kg to 60 mg/kg of the albiflorin are used.

10. A method for treating sepsis, comprising: administering a drug prepared from the pharmaceutical composition according to claim 4 to a patient in need.

* * * * *